United States Patent
Jung et al.

(10) Patent No.: US 7,018,204 B2
(45) Date of Patent: *Mar. 28, 2006

(54) METHODS FOR DETERMINING OPTICAL CHARACTERISTICS OF DENTAL OBJECTS USING AN IMAGING ELEMENT AND A SPECTROMETER APPARATUS

(75) Inventors: Wayne D. Jung, Morton Grove, IL (US); Russell W. Jung, Morton Grove, IL (US); Alan R. Loudermilk, Chicago, IL (US)

(73) Assignee: JJL Technologies LLC, Morton Grove, IL (US)

( * ) Notice: Subject to any disclaimer, the term of this patent is extended or adjusted under 35 U.S.C. 154(b) by 438 days.

This patent is subject to a terminal disclaimer.

(21) Appl. No.: 09/872,071

(22) Filed: Jun. 1, 2001

(65) Prior Publication Data

US 2001/0029009 A1 Oct. 11, 2001

Related U.S. Application Data

(63) Continuation of application No. 08/909,664, filed on Aug. 12, 1997, now Pat. No. 6,264,470, which is a continuation of application No. 08/582,054, filed on Jan. 2, 1996, now Pat. No. 5,759,030.

(51) Int. Cl.
*A61C 19/10* (2006.01)

(52) U.S. Cl. .......................................... 433/26; 356/73
(58) Field of Classification Search ................ 433/26, 433/29, 203.1, 116; 600/125, 124, 182, 477, 600/478; 356/73, 371, 402, 405, 406, 407
See application file for complete search history.

(56) References Cited

U.S. PATENT DOCUMENTS

| | | |
|---|---|---|
| 3,327,584 A | 6/1967 | Kissinger |
| 3,436,157 A | 4/1969 | Adler et al. |
| 3,507,042 A | 4/1970 | Hana |
| 3,555,262 A | 1/1971 | Shimada |

(Continued)

FOREIGN PATENT DOCUMENTS

| | | |
|---|---|---|
| DE | 2256355 | 12/1973 |
| EP | 0167750 | 1/1986 |
| EP | 0681256 | 11/1995 |

(Continued)

OTHER PUBLICATIONS

Aswell, Cecil J. et al., "A Monolithic Light–to–Frequency Converter with a Scalable Sensor Array", IEEE, 1994, pp. 122–123 and 158–159.

Bangston et al.; "The conversion of Chromascan designations to CIE tristimilus values"; Nov. 1982; pp 610–617 vol. 48 No. 5, Journal of Prosthetic Dentistry.

(Continued)

*Primary Examiner*—Ralph A. Lewis
(74) *Attorney, Agent, or Firm*—Loudermilk & Associates

(57) ABSTRACT

Color measuring systems and methods such as for determining the color or other characteristics of teeth are disclosed. Perimeter receiver fiber optics are spaced apart from a central source fiber optic and receive light reflected from the surface of the object/tooth being measured. Light from the perimeter fiber optics pass to a variety of filters. The system utilizes the perimeter receiver fiber optics to determine information regarding the height and angle of the probe with respect to the object/tooth being measured. Under processor control, the color measurement may be made at a predetermined height and angle. Various color spectral photometer arrangements are disclosed. Translucency, fluorescence and/or surface texture data also may be obtained. Audio feedback may be provided to guide operator use of the system. The probe may have a removable or shielded tip for contamination prevention. A method of producing dental prostheses based on measured data also is disclosed. Measured data also may be stored and/or organized as part of a patient data base.

120 Claims, 20 Drawing Sheets

U.S. PATENT DOCUMENTS

| | | | |
|---|---|---|---|
| 3,743,429 A | 7/1973 | Kawai | |
| 3,748,741 A | 7/1973 | Yerkes, Jr. | |
| 3,778,541 A | 12/1973 | Bowker | |
| 3,940,608 A | 2/1976 | Kissinger | |
| 3,986,777 A | 10/1976 | Roll | |
| 4,054,389 A | 10/1977 | Owen | |
| 4,115,922 A | 9/1978 | Alderman | |
| 4,125,329 A | 11/1978 | French et al. | |
| 4,184,175 A | 1/1980 | Mullane, Jr. | |
| 4,207,678 A | 6/1980 | Jeannette | |
| 4,241,738 A | 12/1980 | Lübbers et al. | |
| 4,278,353 A | 7/1981 | Ostermayer et al. | |
| 4,290,433 A | 9/1981 | Alfano | |
| 4,324,546 A | 4/1982 | Heitlinger et al. | |
| 4,382,784 A | 5/1983 | Freller | |
| 4,411,626 A | 10/1983 | Becker et al. | |
| 4,434,654 A | 3/1984 | Hulsing, II et al. | |
| 4,464,054 A | 8/1984 | Karras et al. | |
| 4,487,206 A | 12/1984 | Aagard | |
| 4,505,589 A | 3/1985 | Ott et al. | |
| 4,560,275 A | 12/1985 | Goetz | |
| 4,568,191 A | 2/1986 | Barry | |
| 4,575,805 A | 3/1986 | Moermann et al. | |
| 4,616,933 A | 10/1986 | Leveque et al. | |
| 4,654,794 A | 3/1987 | O'Brien | |
| 4,666,309 A | 5/1987 | Barry et al. | |
| 4,687,329 A | 8/1987 | Schultz | |
| 4,707,138 A | 11/1987 | Coatney | |
| 4,728,290 A | 3/1988 | Eisner et al. | |
| 4,730,922 A | 3/1988 | Bach et al. | |
| 4,773,063 A | 9/1988 | Hunsperger et al. | |
| 4,798,951 A | 1/1989 | Walker | |
| 4,823,169 A | 4/1989 | Ogura | |
| 4,836,674 A | 6/1989 | Lequime et al. | |
| 4,844,617 A | 7/1989 | Kelderman et al. | |
| 4,878,485 A | 11/1989 | Adair | |
| 4,881,811 A | 11/1989 | O'Brien | |
| 4,914,512 A | 4/1990 | Sekiguchi | |
| 4,917,500 A | 4/1990 | Lugos | |
| 4,957,371 A | 9/1990 | Pellicori et al. | |
| 4,966,458 A | 10/1990 | Burns et al. | |
| 4,986,671 A | 1/1991 | Sun et al. | |
| 4,988,206 A | 1/1991 | Melleney et al. | |
| 5,017,772 A | 5/1991 | Hafle | |
| 5,028,139 A | 7/1991 | Kramer et al. | |
| 5,040,940 A | 8/1991 | Kolodziej et al. | |
| 5,095,210 A | 3/1992 | Wheatley et al. | |
| 5,139,335 A | 8/1992 | Lundeen et al. | |
| 5,142,383 A | 8/1992 | Mallik | |
| 5,159,199 A | 10/1992 | LaBaw | |
| 5,164,597 A | 11/1992 | Lodder | |
| 5,166,755 A | 11/1992 | Gat | |
| 5,193,525 A | 3/1993 | Silverstein | |
| 5,229,841 A | 7/1993 | Taranowski et al. | |
| 5,245,404 A | 9/1993 | Jannson et al. | |
| 5,306,144 A | 4/1994 | Hibst et al. | |
| 5,308,771 A | 5/1994 | Zhou et al. | |
| 5,309,256 A | 5/1994 | Takada et al. | |
| 5,329,935 A | 7/1994 | Takahashi | |
| 5,369,481 A | 11/1994 | Berg et al. | |
| 5,371,586 A | 12/1994 | Chau | |
| 5,372,502 A * | 12/1994 | Massen et al. | 433/215 |
| 5,377,669 A | 1/1995 | Schultz | |
| 5,383,020 A | 1/1995 | Vieillefosse | |
| 5,386,292 A | 1/1995 | Massen et al. | |
| 5,392,110 A | 2/1995 | Yojima et al. | |
| 5,401,954 A | 3/1995 | Richert | |
| 5,401,967 A | 3/1995 | Stedman et al. | |
| 5,404,218 A | 4/1995 | Nave et al. | |
| 5,410,410 A | 4/1995 | Yamazaki et al. | |
| 5,410,413 A | 4/1995 | Sela | |
| 5,428,450 A | 6/1995 | Vieillefosse et al. | |
| 5,450,193 A | 9/1995 | Carlsen et al. | |
| 5,450,203 A | 9/1995 | Penkethman | |
| 5,450,511 A | 9/1995 | Dragone | |
| 5,453,838 A | 9/1995 | Danielian et al. | |
| 5,457,525 A | 10/1995 | Ohtsuka et al. | |
| 5,461,476 A | 10/1995 | Fournier | |
| 5,467,289 A | 11/1995 | Abe et al. | |
| 5,469,249 A | 11/1995 | Magyar, Jr., et al. | |
| 5,474,449 A | 12/1995 | Loge et al. | |
| 5,477,332 A | 12/1995 | Stone et al. | |
| 5,483,335 A | 1/1996 | Tobias | |
| 5,487,661 A | 1/1996 | Peithman | |
| 5,497,227 A | 3/1996 | Takeuchi et al. | |
| 5,498,157 A | 3/1996 | Hall | |
| 5,533,628 A | 7/1996 | Tao | |
| 5,560,355 A | 10/1996 | Merchant et al. | |
| 5,565,976 A | 10/1996 | Fieggen et al. | |
| 5,575,284 A | 11/1996 | Athan et al. | |
| 5,583,631 A | 12/1996 | Lazzerini | |
| 5,590,251 A | 12/1996 | Takagi | |
| 5,592,294 A | 1/1997 | Ota et al. | |
| 5,604,594 A | 2/1997 | Juffinger | |
| 5,609,978 A | 3/1997 | Giorgianni et al. | |
| 5,625,459 A | 4/1997 | Driver | |
| 5,668,633 A | 9/1997 | Cheetam et al. | |
| 5,671,735 A | 9/1997 | MacFarlane et al. | |
| 5,683,243 A | 11/1997 | Andreiko et al. | |
| 5,690,486 A | 11/1997 | Zigelbaum | |
| 5,695,949 A | 12/1997 | Galen et al. | |
| 5,696,751 A | 12/1997 | Juffinger | |
| 5,742,060 A | 4/1998 | Ashburn | |
| 5,745,229 A | 4/1998 | Jung et al. | |
| 5,754,283 A | 5/1998 | Keane et al. | |
| 5,757,496 A | 5/1998 | Yamazaki | |
| 5,759,030 A | 6/1998 | Jung et al. | |
| 5,766,006 A | 6/1998 | Murljacic | |
| 5,774,610 A | 6/1998 | O'Rourke et al. | |
| 5,784,507 A | 7/1998 | Holm-Kennedy et al. | |
| 5,798,839 A | 8/1998 | Berner et al. | |
| 5,822,474 A | 10/1998 | Hara | |
| 5,850,195 A | 12/1998 | Berlien, Jr. et al. | |
| 5,850,301 A | 12/1998 | Mizuochi et al. | |
| 5,880,826 A | 3/1999 | Jung et al. | |
| 5,883,708 A | 3/1999 | Jung et al. | |
| 5,924,981 A | 7/1999 | Rothfritz et al. | |
| 5,926,262 A * | 7/1999 | Jung et al. | 356/73 |
| 5,961,324 A | 10/1999 | Lehmann | |
| 5,961,327 A | 10/1999 | Lohn | |
| 5,989,022 A | 11/1999 | Yamamoto et al. | |
| 5,995,235 A | 11/1999 | Sui et al. | |
| 6,002,488 A | 12/1999 | Berg et al. | |
| 6,007,332 A | 12/1999 | O'Brien | |
| 6,008,905 A | 12/1999 | Breton et al. | |
| 6,030,209 A | 2/2000 | Panzera et al. | |
| 6,031,928 A | 2/2000 | Scott | |
| 6,038,024 A | 3/2000 | Berner | |
| 6,040,902 A | 3/2000 | Jung et al. | |
| 6,052,195 A | 4/2000 | Mestha et al. | |
| 6,057,925 A | 5/2000 | Anthon | |
| 6,086,274 A | 7/2000 | Krzyminski | |
| 6,188,471 B1 * | 2/2001 | Jung et al. | 356/73 |
| 6,222,620 B1 * | 4/2001 | Jung et al. | 356/73 |
| 6,249,340 B1 * | 6/2001 | Jung et al. | 356/73 |
| 6,254,385 B1 * | 7/2001 | Jung et al. | 433/26 |
| 6,264,470 B1 * | 7/2001 | Jung et al. | 433/29 |
| 6,573,984 B1 * | 6/2003 | Jung et al. | 356/73 |

FOREIGN PATENT DOCUMENTS

| FR | 2669526 | | 5/1992 |
|---|---|---|---|
| JP | 54103055 | | 8/1979 |
| WO | 8603292 | | 6/1986 |
| WO | WO 97/24075 | * | 7/1997 |

OTHER PUBLICATIONS

Barghi et al.; "Effects of batch variation on shade of dental porcelain"; Nov. 1985; pp 625–627, vol. 54 No. 5, Journal of Prosthetic Dentistry.

Council on Dental Materials, Instruments, and Equipment; "How to improve shade matching in the dental operatory"; Feb. 1981; pp 209–210, vol. 102; JADA.

Davison et al.; "Shade selection by color vision-defective dental personnel"; Jan. 1990; pp 97–101 vol. 63 No. 1, Journal of Prosthetic Dentistry.

Demro, James C., R. Hartshome, P.A. Levine, L.M. Woody, "Design of Multispectral, Wedge Filter, Remote–Sensing Instrument incorporating a multi–port, thinned, CCD area array" SPIE vol. 2480 p. 280.

Dickerson, "Trilogy of Creating an Esthetic Smile"; Jul. 1996; pp 1–7, vol. 1, Issue 3; Technical Update–A Publication of Micro Dental Laboratories.

Elerding, George T. John G. Thunen, Loren M. Woody "Wedge Imaging Spectrometer: Application to drug and pollution law enforcement" SPIE vol. 1479 *Surveillance Technologies*, p. 380 (1991).

Goldstein et al.; "Repeatability of a specially designed intraoral colorimeter"; Jun. 1993; pp 616–619, vol. 69 No. 6, Journal of Prosthetic Dentistry.

Goodkind et al.; "A comparison of Chromascan and spectrophotometric color measurement of 100 natural teeth"; Jan. 1985; pp 105–109, vol. 53 No. 1, Journal of Prosthetic Dentistry.

Ishikawa et al.; "Trial Manufacture of Photoelectric Colorimeter Using Optical Fibers"; Nov. 1969; pp 191–197, vol. 10, No. 4, Bull. Tokyo dent. Coll.

Johnston et al.; "The Color Accuracy of the Kubelka–Munk Theory for Various Colorants in Maxillofacial Prosthetic Material"; Sep. 1987; pp 1438–1444, vol. 66, No. 9; J. Dent. Res.

Johnston et al.; "Assessment of Appearance Match by Visual Observation and Clinical Colorimetry"; May 1989; pp 819–822, vol. 68, No. 5; J. Dent. Res.

Kato et al; "The Current State of Porcelain Shades: A Discussion"; Oct. 1984; pp 559–571, vol. 8, No. 9; Quintessence Of Dental Technology.

Mika, Aram M., "Linear–Wedge Spectrometer" SPIE vol. 1298 *Imaging Spectroscopy of the Terrestrial Environment*, p. 127 (1990).

Miller; "Organizing color in dentistry"; Dec. 1987; pp 26E–40E, Special Issue; JADA.

Miller et al; "Shade selection and laboratory communication"; May 1993; pp 305–309, vol. 24, No. 5; Quintessence International.

O'Brien et al.; "Coverage Errors of Two Shade Guides"; Jan./Feb. 1991; pp 45–50, vol. 4, No. 1; The International Journal of Prosthodontics.

O'Brien et al.; "A New, Small–color–difference Equation for Dental Shades"; Nov. 1990; pp 1762–1764, vol. 69, No. 11; J. Dent. Res.

O'Keefe et al.; "Color Shade and Matching: The Weak Link in Esthetic Dentistry"; Feb. 1990; pp 116–120, vol. XI, No. 2, Compend Contin Educ Dent.

Pensler; "A New Approach to Shade Selection"; Sep. 1991; pp 668–675, vol. XII, No. 9, Compend Contin Educ Dent.

Preston et al.; "Light and Lighting in the Dental Office"; Jul. 1978; pp 431–451, vol. 22, No. 3; Dental Clinics of North America.

Preston; "Current status of shade selection and color matching"; Jan. 1985; pp 47–58, vol. 16, No. 1; Quintessence International.

Rosenstiel et al.; "The effects of manipulative variables on the color of ceramic metal restorations"; Sep. 1987; pp 297–303, vol. 60 No. 3, Journal of Prosthetic Dentistry.

Rugh et al.; "The Relationship Between Elastomer Opacity, Colorimeter Beam Size, and Measured Colorimetric Response"; Nov./Dec. 1991; pp 569–576, vol. 4, No. 6; The International Journal of Prosthodontics.

Ryther et al.; "Colormetric Evaluation of Shade Guide Variability"; 1993; p. 215; J. Dent. Res. 72 (IADR Abstracts) Special Issue.

Schwabacher et al.; "Three–dimensional color coordinates of natural teeth compared with three shade guides"; Oct. 1990; pp 425–431, vol. 64 No. 4, Journal of Prosthetic Denstistry.

Seghi et al.; "Spectrophotometric analysis of color differences between porcelain systems"; Jul. 1986; pp 35–40, vol. 56 No. 1, Journal of Prosthetic Dentistry.

Seghi et al.; "Visual and Instrumental Colorimetric Assessments of Small Color Differences on Translucent Dental Porcelain"; Dec. 1989; pp 1760–1764 vol. 68, No. 12; J. Dent. Res.

Seghi et al., "Performance Assessment of Colorimetric Devices on Dental Porcelains"; Dec. 1989; pp 1755–1759, vol. 69, No. 11; J. Dent. Res.

Seghi; "Effects of Instrument–measuring Geometry on Colorimetric Assessments of Dental Porcelains"; May 1990; pp 1180–1183, vol. 69, No. 5; J. Dent. Res.

Sorensen et al.; "Improved color matching of metal–ceramic restorations. Part I: A systematic method for shade determination"; Aug. 1987; pp 133–139, vol. 58, No. 2, Journal of Prosthetic Dentistry.

Sorensen et al.; "Improved color matching of metal–ceramic restorations. Part II: Procedures for visual communication"; Dec. 1987; pp 669–677, vol. 58, No. 6, Journal of Prosthetic Dentistry.

Sproul; "Color matching in dentistry. Part I. The three–dimensional nature of color"; Apr. 1973; pp 416–424, vol. 29, No. 4; J. Prosthet. Dent.

Sproul; "Color matching in dentistry. Part I. Color control"; Feb. 1974; pp 146–154, vol. 31, No. 2; J. Prosthet. Dent.

Sproul; "Color matching in dentistry. Part 2. Practical applications of the organization of color"; May 1973; pp 556–566, vol. 29, No. 5; J. Prosthet. Dent.

Swift et al.; "Colormetric Evaluation of Vita Shade Resin Composites"; 1994; pp 356–361, vol. 7, No. 4; The International Journal of Prosthodontics.

van der Burgt et al.; "A comparison of new and conventional methods for quantification of tooth color"; Feb. 1990; pp 155–162, vol. 63 No. 2, Journal of Prosthetic Dentistry.

* cited by examiner

R - LIGHT RECEIVER FIBER OPTICS
S - LIGHT SOURCE FIBER OPTIC

S - LIGHT SOURCE FIBER
R - RED RECEIVER
G - GREEN RECEIVER
B - BLUE RECEIVER
P - NEUTRAL (FULL BAND) RECEIVERS

S - LIGHT SOURCE FIBER
P - NEUTRAL (FULL BAND) RECEIVER
C - COLOR RECEIVER

S - LIGHT SOURCE FIBER
$R_{1X}$ - INNER RING RECEIVER FIBER
$R_{2X}$ - 2nd RING RECEIVER FIBER
$R_{3X}$ - 3rd RING RECEIVER FIBER

SINGLE FILTER PROPERTIES (SPECTRUM)

INTRAORAL POSITIONING DEVICE

METHODS FOR DETERMINING OPTICAL CHARACTERISTICS OF DENTAL OBJECTS USING AN IMAGING ELEMENT AND A SPECTROMETER APPARATUS

This is a continuation of U.S. application Ser. No. 08/909,664, filed Aug. 12, 1997, now U.S. Pat. No. 6,264,470, which is a continuation of application Ser. No. 08/582,054 filed Jan. 2, 1996, now U.S. Pat. No. 5,759,030.

FIELD OF THE INVENTION

The present invention relates to devices and methods for measuring the color of objects such as teeth, and more particularly to devices and methods for measuring the color of teeth or other objects or surfaces with a hand-held probe that presents minimal problems with height or angular dependencies.

BACKGROUND OF THE INVENTION

A need has been recognized for devices and methods of measuring the color of teeth and other objects in the field of dentistry. Various color measuring devices such as spectrophotometers and colorimeters are known in the art. To understand the limitations of such conventional devices, it is helpful to understand certain principles relating to color. Without being bound by theory, Applicants provide the following discussion. In the discussion herein, reference is made to an "object," etc., and it should be understood that in general such discussion may include teeth as the "object."

The color of an object determines the manner in which light is reflected from the surface of the object. When light is incident upon an object, the reflected light will vary in intensity and wavelength dependent upon the color of the surface of the object. Thus, a red object will reflect red light with a greater intensity than a blue or a green object, and correspondingly a green object will reflect green light with a greater intensity than a red or blue object.

One method of quantifying the color of an object is to illuminate it with broad band spectrum or "white" light, and measure the spectral properties of the reflected light over the entire visible spectrum and compare the reflected spectrum with the incident light spectrum. Such instruments typically require a broad band spectrophotometer, which generally are expensive, bulky and relatively cumbersome to operate, thereby limiting the practical application of such instruments.

For certain applications, the broad band data provided by a spectrophotometer is unnecessary. For such applications, devices have been produced or proposed that quantify color in terms of a numerical value or relatively small set of values representative of the color of the object.

It is known that the color of an object can be represented by three values. For example, the color of an object can be represented by red, green and blue values, an intensity value and color difference values, by a CIE value, or by what are known as "tristimulus values" or numerous other orthogonal combinations. It is important that the three values be orthogonal; i.e., any combination of two elements in the set cannot be included in the third element.

One such method of quantifying the color of in object is to illuminate an object with broad, band "white" light and measure the intensity of the reflected light after it has been passed through narrow band filters. Typically three filters (such as red, green and blue) are used to provide tristimulus light values representative of the color of the surface. Yet another method is to illuminate an object with three monochromatic light sources (such as red, green and blue) one at a time and then measure the intensity of the reflected light with a single light sensor. The three measurements are then converted to a tristimulus value representative of the color of the surface. Such color measurement techniques can be utilized to produce equivalent tristimulus values representative of the color of the surface. Generally, it does not matter if a "white" light source is used with a plurality of color sensors (or a continuum in the case of a spectrophotometer), or if a plurality of colored light sources are utilized with a single light sensor.

There are, however, difficulties with the conventional techniques. When light is incident upon a surface and reflected to a light receiver, the height of the light sensor and the angle of the sensor relative to the surface and to the light source also affect the intensity of the received light. Since the color determination is being made by measuring and quantifying the intensity of the received light for different colors, it is important that the height and angular dependency of the light receiver be eliminated or accounted for in some manner.

One method for eliminating the height and angular dependency of the light source and receiver is to provide a fixed mounting arrangement where the light source and receiver are stationary and the object is always positioned and measured at a preset height and angle. The fixed mounting arrangement greatly limits the applicability of such a method. Another method is to add mounting feet to the light source and receiver probe and to touch the object with the probe to maintain a constant height and angle. The feet in such an apparatus must be wide enough apart to insure that a constant angle (usually perpendicular) is maintained relative to the object. Such an apparatus tends to be very difficult to utilize on small objects or on objects that are hard to reach, and in general does not work satisfactorily in measuring objects with curved surfaces. Such devices are particularly difficult to implement in the field of dentistry.

The use of color measuring devices in the field of dentistry has been proposed. In modern dentistry, the color of teeth typically are quantified by manually comparing a patient's teeth with a set of "shade guides." There are numerous shade guides available for dentists in order to properly select the desired color of dental prosthesis. Such shade guides have been utilized for decades and the color determination is made subjectively by the dentist by holding a set of shade guides next to a patient's teeth and attempting to find the best match. Unfortunately, however, the best match often is affected by the ambient light color in the dental operatory and the surrounding color of the patient's makeup or clothing and by the fatigue level of the dentist. In addition, such pseudo trial and error methods based on subjective matching with existing industry shade guides for forming dental prostheses, fillings and the like often result in unacceptable color matching, with the result that the prosthesis needs to be remade, leading to increased costs and inconvenience to the patient, dental professional and/or prosthesis manufacturer.

Similar subjective color quantification also is made in the paint industry by comparing the color of an object with a paint reference guide. There are numerous paint guides available in the industry and the color determination also often is affected by ambient light color, user fatigue and the color sensitivity of the user. Many individuals are color insensitive (color blind) to certain colors, further complicating color determination.

While a need has been recognized in the field of dentistry, however, the limitations of conventional color measuring techniques typically restrict the utility of such techniques. For example, the high cost and bulkiness of typical broad band spectrometers, and the fixed mounting arrangements or feet required to address the height and angular dependency, often limit the applicability of such conventional techniques.

Moreover, another limitation of such conventional methods and devices are that the resolution of the height and angular dependency problems typically require contact with the object being measured. In certain applications, it may be desirable to measure and quantify the color of an object with a small probe that does not require contact with the surface of the object. In certain applications, for example, hygienic considerations make such contact undesirable. In the other applications, contact with the object can mar the surface (such as if the object is coated in some manner) or otherwise cause undesirable effects.

In summary, there is a need for a low cost, hand-held probe of small size that can reliably measure and quantify the color of an object without requiring physical contact with the object, and also a need for methods based on such a device in the field of dentistry and other applications.

SUMMARY OF THE INVENTION

In accordance with the present invention, devices and methods are provided for measuring the color of objects such as teeth, reliably and with minimal problems of height and angular dependence. A handheld probe is utilized in the present invention, with the handheld probe containing a number of fiber optics. Light is directed from one (or more) light source fiber optics towards the object/tooth to be measured, which in certain preferred embodiments is a central light source fiber optic (other light source arrangements also may be utilized). Light reflected from the object is detected by a number of light receiver fiber optics. Included in the light receiver fiber optics are a plurality of perimeter fiber optics. In certain preferred embodiments, three perimeter fiber optics are utilized in order to take measurements at a desired, and predetermined height and angle, thereby minimizing height and angular dependency problems found in conventional methods. In certain embodiments, the present invention also may measure translucence and fluorescence characteristics of the object/tooth being measured, as well as surface texture and/or other surface characteristics.

The present invention may include constituent elements of a broad band spectrophotometer, or, alternatively, may include constituent elements of a tristimulus type colorimeter. The present invention may employ a variety of color measuring devices in order to measure color in a practical, reliable and efficient manner, and in certain preferred embodiments includes a color filter array and a plurality of color sensors. A microprocessor is included for control and calculation purposes. A temperature sensor is included to measure temperature in order to detect abnormal conditions and/or to compensate for temperature effects of the filters or other components of the system. In addition, the present invention may include audio feedback to guide the operator in making color measurements, as well is one or more display devices for displaying control, status or other information.

With the present invention, color measurements of teeth or the like may be made with a handheld probe in a practical and reliable manner, essentially free of height and angular dependency problems, without resorting to fixtures, feet or other undesirable mechanical arrangements for fixing the height and angle of the probe with respect to the object/tooth. In addition, the present invention includes methods of using such color measurement data to implement processes for forming dental prostheses and the like, as well as methods for keeping such color and/or other data as part of a patient record database.

Accordingly, it is an object of the present invention to address limitations of conventional color measuring techniques.

It is another object of the present invention to provide a method and device useful in measuring the color of teeth or other objects or surfaces with a hand-held probe of practical size that does not require contact with the object or surface.

It is a further object of the present invention to provide a color measurement probe and method that does not require fixed position mechanical mounting, feet or other mechanical impediments.

It is yet another object of the present invention to provide a probe and method useful for measuring color that may be utilized with a probe simply placed near the surface to be measured.

It is a still further object of the present invention to provide a probe and method that are capable of determining translucency characteristics of the object being measured.

It is a further object of the present invention to provide a probe and method that are capable of determining surface texture characteristics of the object/tooth being measured.

It is a still further object of the present invention to provide a probe and method that are capable of determining fluorescence characteristics of the object/tooth being measured.

It is another object of the present invention to provide a probe and method that can measure the area of a small spot singulary, or that also can measure the color of irregular shapes by moving the probe over an area and integrating the color of the entire area.

It is a further object of the present invention to provide a method of measuring the color of teeth and preparing dental prostheses, dentures, intraoral tooth-colored fillings or other materials.

It is yet another object of the present invention to provide a method and apparatus that minimizes contamination problems, while providing a reliable and expedient manner in which to measure teeth and prepare dental prostheses, dentures, intraoral tooth-colored fillings or other materials.

Finally, it is an object of the present invention to provide methods of using measured data to implement processes for forming dental prostheses and the like, as well as methods for keeping such measurement and/or other data as part of a patient record database.

BRIEF DESCRIPTION OF THE DRAWINGS

The present invention may be more fully understood by a description of certain preferred embodiments in conjunction with the attached drawings in which.

DETAILED DESCRIPTION OF THE PREFERRED EMBODIMENTS

The present invention will be described in greater detail with reference to certain preferred embodiments. At various places herein, reference is made to an "object," for example. It should be understood that an exemplary use of the present invention is in the field of dentistry, and thus the object typically should be understood to include teeth, dentures, dental-type cements or the like, although for discussion purposes in certain instances reference is only made to the "object."

Figure 1:
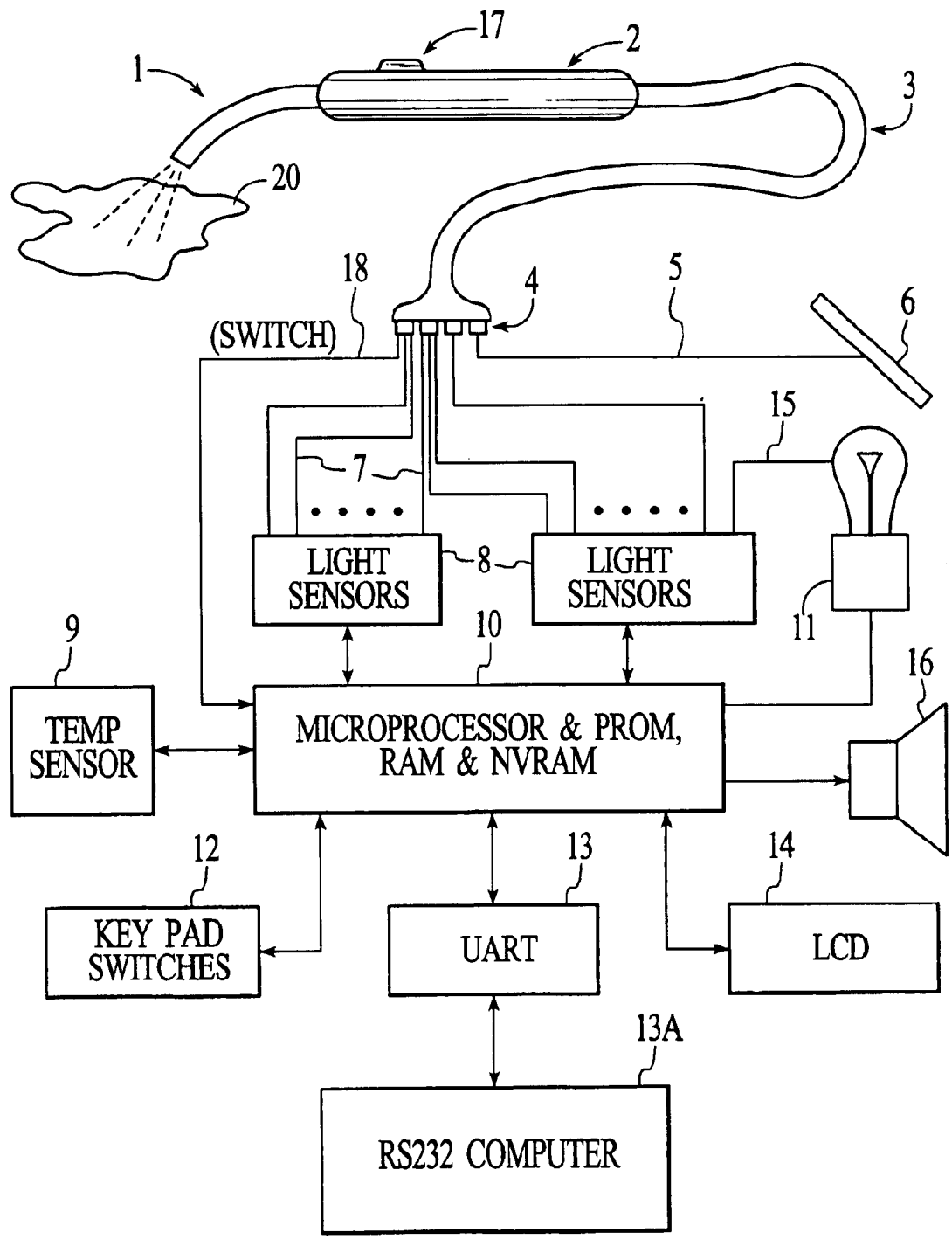
FIG. 1 is a diagram illustrating a preferred embodiment of the present invention.

With reference to FIG. 1, an exemplary preferred embodiment of a color measuring system and method in accordance with the present invention will be described.

Probe tip 1 encloses a plurality of fiber optics, each of which may constitute one or more fiber optic fibers. In a preferred embodiment, the fiber optics contained within probe tip 1 includes a single light source fiber optic and three light receiver fiber optics. The use of such fiber optics to measure the color of an object will be described later herein. Probe tip 1 is attached to probe body 2, on which is fixed switch 17. Switch 17 communicates with microprocessor 10 through wire 18 and provides, for example, a mechanism by which an operator may activate the device in order to make a color measurement. Fiber optics within probe tip 1 terminate at the forward end thereof (i.e., the end away from probe body 2). The forward end of probe tip 1 is directed towards the surface of the object to be measured as described more fully below. The fiber optics within probe tip 1 optically extend through probe body 2 and through fiber optic cable 3 to light sensors 8, which are coupled to microprocessor 10.

It should be noted that microprocessor 10 includes conventional associated components, such as memory (programmable memory, such as PROM, EPROM or EEPROM; working memory such as DRAMs or SRAMs; and/or other types of memory such as non-volatile memory, such as FLASH), peripheral circuits, clocks and power supplies, although for clarity such components are not explicitly shown. Other types of computing devices (such as other microprocessor systems, programmable logic arrays or the like) are used in other embodiments of the present invention.

In the embodiment of FIG. 1, the fiber optics from fiber optic cable 3 end at splicing connector 4. From splicing connector 4, each of the three receiver fiber optics used in this embodiment is spliced into at least five smaller fiber optics ((generally denoted as fibers 7), which in this embodiment are fibers of equal diameter, but which in other embodiments may be of unequal diameter (such as a larger or smaller "height/angle" or perimeter fiber, as more fully described herein). One of the fibers of each group of five fibers passes to light sensors 8 through a neutral density filter (as more fully described with reference to FIG. 3), and collectively such neutrally filtered fibers are utilized for purposes of height/angle determination (and also may be utilized to measure surface characteristics, as more fully described herein). Four of the remaining fibers of each group of fibers passes to light sensors 8 through color filters and are used to make the color measurement. In still other embodiments, splicing connector 4 is not used, and fiber bundles of, for example, five or more fibers each extend from light sensors 8 to the forward end of probe tip 1. In certain embodiments, unused fibers or other materials may be included as part of a bundle of fibers for purposes of, for example, easing the manufacturing process for the fiber bundle. What should be noted is that, for purposes of the present invention, a plurality of light receiver fiber optics (such as fibers 7) are presented to light sensors 8, with the light from the light receiver fiber optics representing light reflected from object 20. While the various embodiments describe herein present tradeoffs and benefits that may not have been apparent prior to the present invention (and thus may be independently novel), what is important for the present discussion is that light from fiber optics at the forward end of probe tip 1 is presented to color sensors 8 for color measurement and angle/height determination, etc.

Light source 11 in the preferred embodiment is a halogen light source (of, for example, 5–100 watts, with the particular wattage chosen for the particular application), which may be under the control of microprocessor 10. The light from light source 11 reflects from cold mirror 6 and into source fiber optic 5. Source fiber optic 5 passes through to the forward end of probe tip 1 and provides the light stimulus used for purposes of making the measurements described herein. Cold mirror 6 reflects visible light and passes infra-red light, and is used to reduce the amount of infra-red light produced by light source 11 before the light is introduced into source fiber optic 5. Such infra-red light reduction of the light from a halogen source such as light source 11 can help prevent saturation of the receiving light sensors, which can reduce overall system sensitivity. Fiber 15 receives light directly from light source 11 and passes through to light sensors 8 (which may be through a neutral density filter). Microprocessor 10 monitors the light output of light source 11 through fiber 15, and thus may monitor and, if necessary compensate for, drift of the output of light source 11. In certain embodiments, microprocessor 10 also may sound an alarm (such as through speaker 16) or otherwise provide some indication if abnormal or other undesired performance of light source 11 is detected.

The data output from light sensors 8 pass to microprocessor 10. Microprocessor 10 processes the data from light sensors 8 to produce a measurement of color and/or other characteristics. Microprocessor 10 also is coupled to key pad switches 12, which serve as an input device. Through key pad switches 12, the operator may input control information or commands, or information relating to the object being measured or the like. In general, key pad switches 12, or other suitable data input devices (such as push button, toggle, membrane or other switches or the like), serve as a mechanism to input desired information to microprocessor 10.

Microprocessor 10 also communicates with UART 13, which enables microprocessor 10 to be coupled to an external device such as computer 13A. In such embodiments, color data provided by microprocessor 10 may be processed as desired for the particular application, such as for averaging, format conversion or for various display or print options, etc. In the preferred embodiment, UART 13 is configured so as to provide what is known as a RS232 interface, such as is commonly found in personal computers.

Microprocessor 10 also communicates with LCD 14 for purposes of displaying status, control or other information as desired for the particular application. For example, color bars, charts or other graphic representations of the color or other collected data and/or the measured object or tooth may be displayed. In other embodiments, other display devices are used, such as CRTs, matrix-type LEDs, lights or other mechanisms for producing a visible indicia of system status or the like. Upon system initialization, for example, LCD 14 may provide an indication that the system is stable, ready and available for taking color measurements.

Also coupled to microprocessor 10 is speaker 16. Speaker 16, in a preferred embodiment as discussed more fully below, serves to provide audio feedback to the operator, which may serve to guide the operator in the use of the device. Speaker 16 also may serve to provide status or other information altering the operator of the condition of the system, including an audio tone, beeps or other audible indication (i.e., voice) that the system is initialized and available for taking measurements. Speaker 16 also may present audio information indicative of the measured data, shade guide or reference values corresponding to the measured data, or an indication of the status of the color measurements.

Microprocessor 10 also receives an input from temperature sensor 9. Given that many types of filters (and perhaps light sources or other components) may operate reliably only in a given temperature range, temperature sensor 9 serves to provide temperature information to microprocessor 10. In particular, color filters, such as may be included in light sensors 8, are sensitive to temperature, and operate reliably only over a certain temperature range. In certain embodiments, if the temperature is within a usable range, microprocessor 10 may compensate for temperature variations of the color filters. In such embodiments, the color filters are characterized as to filtering characteristics as a function of temperature, either by data provided by the filter manufacturer, or through measurement as a function of temperature. Such filter temperature compensation data may be stored in the form of a look-up table in memory, or may be stored as a set of polynomial coefficients from which the temperature characteristics of the filters may be computed by microprocessor 10.

In general, under control of microprocessor 10, which may be in response to operator activation (through, for example, key pad switches 12 or switch 17), light is directed from light source 11, and reflected from cold mirror 6 through source fiber optic 5 (and through fiber optic cable 3, probe body 2 and probe tip 1) and is directed onto object 20. Light reflected from object passes through the receiver fiber optics in probe tip 1 to light sensors 8 (through probe body 2, fiber optic cable 3 and fibers 7). Based on the information produced by light sensors 8, microprocessor 10 produces a color measurement result or other information to the operator. Color measurement or other data produced by microprocessor 10 may be displayed on display 14, passed through UART 13 to computer 13A, or used to generate audio information that is presented to speaker 16. Other operational aspects of the preferred embodiment illustrated in FIG. 1 will be explained hereinafter.

Figure 2:
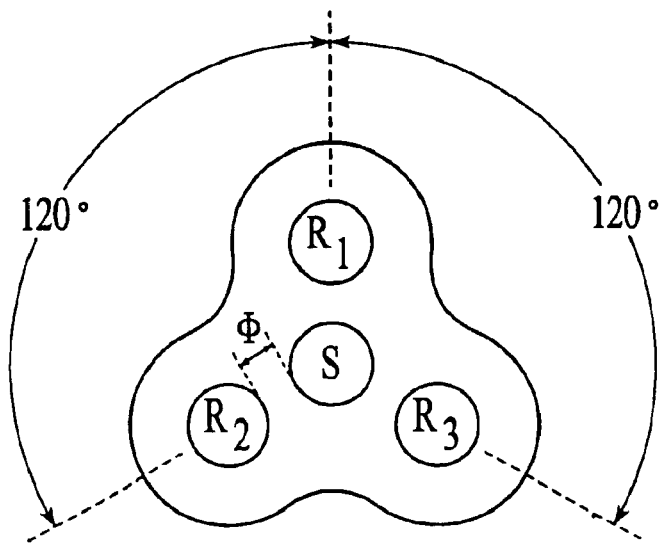
FIG. 2 is a diagram illustrating a cross section of a probe in accordance with a preferred embodiment of the present invention.

With reference to FIG. 2, a preferred embodiment of the fiber optic arrangement presented at the forward end of probe tip 1 will now be described. As illustrated in FIG. 2, a preferred embodiment of the present invention utilizes a single central light source fiber optic, denoted as light source fiber optic S, and a plurality of perimeter light receiver fiber optics, denoted as light receivers R1, R2 and R3. As is illustrated, a preferred embodiment of the present invention utilizes three perimeter fiber optics, although in other embodiments two, four or some other number of receiver fiber optics are utilized. As more fully described herein, the perimeter light receiver fiber optics serve not only to provide reflected light for purposes of making the color measurement, but such perimeter fibers also serve to provide information regarding the angle and height of probe tip 1 with respect to the surface of the object that is being measured, and also may provide information regarding the surface characteristics of the object that is being measured.

In the illustrated preferred embodiment, receiver fiber optics R1 to R3 are positioned symmetrically around source fiber optic S, with a spacing of about 120 degrees from each other. It should be noted that spacing t is provided between receiver fiber optics R1 to R3 and source fiber optic S. While the precise angular placement of the receiver fiber optics around the perimeter of the fiber bundle in general is not critical, it has been determined that three receiver fiber optics positioned 120 degrees apart generally may give acceptable results. As discussed above, in certain embodiments light receiver fiber optics R1 to R3 each constitute a single fiber, which is divided at splicing connector 4 (refer again to FIG. 1), or, in alternate embodiments, light receiver fiber optics R1 to R3 each constitute a bundle of fibers, numbering, for example, at least five fibers per bundle. It has been determined that, with available fibers of uniform size, a bundle of, for example, seven fibers may be readily produced (although as will be apparent to one of skill in the art, the precise number of fibers may be determined in view of the desired number of receiver fiber optics, manufacturing considerations, etc.). The use of light receiver fiber optics R1 to R3 to produce color measurements in accordance with the present invention is further described elsewhere herein, although it may be noted here that receiver fiber optics R1 to R3 may serve to detect whether, for example, the angle of probe tip 1 with respect to the surface of the object being measured is at 90 degrees, or if the surface of the object being measured contains surface texture and/or spectral irregularities. In the case where probe tip 1 is perpendicular to the surface of the object being measured and the surface of the object being measured is a diffuse reflector, then the light intensity input into the perimeter fibers should be approximately equal. It also should be noted that spacing t serves to adjust the optimal height at which color measurements should be made (as more fully described below), and also ensures that the light reflected into receiver fiber optics R1 to R3 is at an angle for diffuse reflection, which helps to reduce problems associated with measurements of "hot spots" on the surface of the object being measured.

In one particular aspect of the present invention, area between the fiber optics on probe tip 1 may be wholly or partially filled with a non-reflective material and/or surface (which may be a black mat, contoured or other non-reflective surface). Having such exposed area of probe tip 1 non-reflective helps to reduce undesired reflections, thereby helping to increase the accuracy and reliability of the present invention.

Figure 3:
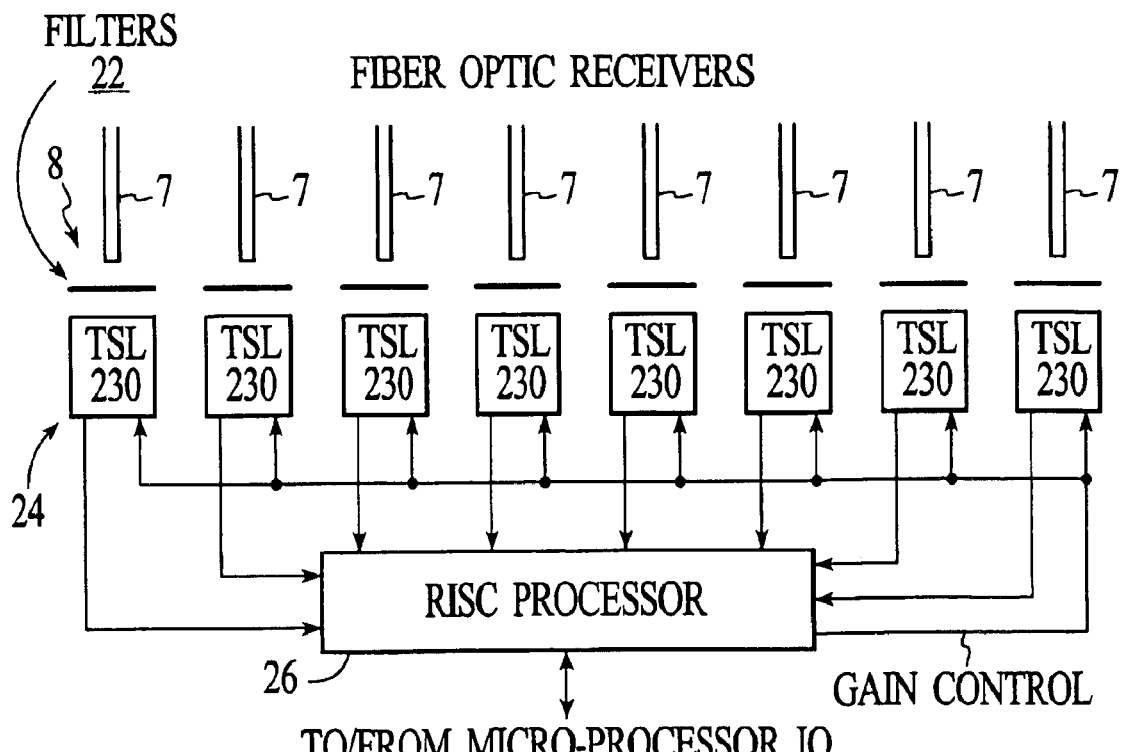
FIG. 3 is a diagram illustrating an arrangement of fiber optic receivers and sensors utilized with a preferred embodiment of the present invention.

With reference to FIG. 3, a partial arrangement of light receiver fiber optics and sensors used in a preferred embodiment of the present invention will now be described. Fibers 7 represent light receiving fiber optics, which transmit light reflected from the object being measured to light sensors 8. In a preferred embodiment, sixteen sensors (two sets of eight) are utilized, although for ease of discussion only 8 are illustrated in FIG. 3 (in this preferred embodiment, the circuitry of FIG. 3 is duplicated, for example, in order to result in sixteen sensors). In other embodiments, other numbers of sensors are utilized in accordance with the present invention.

Light from fibers 7 is presented to sensors 8, which in a preferred embodiment pass through filters 22 to sensing elements 24. In this preferred embodiment, sensing elements 24 include light-to-frequency converters, manufactured by Texas Instruments and sold under the part number TSL230. Such converters constitute, in general, photo diode arrays that integrate the light received from fibers 7 and output an AC signal with a frequency proportional to the intensity (not frequency) of the incident light. Without being bound by theory, the basic principle of such devices is that, as the intensity increases, the integrator output voltage rises more quickly, and the shorter the integrator rise time, the greater the output frequency. The outputs of the TSL230 sensors are TTL or CMOS compatible digital signals, which may be coupled to various digital logic devices.

The outputs of sensing elements 24 are, in this embodiment, asynchronous signals of frequencies depending upon the light intensity presented to the particular sensing elements, which are presented to processor 26. In a preferred embodiment, processor 26 is a Microchip PIC16C55 microprocessor, which as described more fully herein implements an algorithm to measure the frequencies of the signals output by sensing elements 24.

As previously described, processor 26 measures the frequencies of the signals output from sensing elements 24. In a preferred embodiment, processor 26 implements a software timing loop, and at periodic intervals processor 26 reads the states of the outputs of sensing elements 24. An internal counter is incremented each pass through the software timing loop. The accuracy of the timing loop generally is determined by the crystal oscillator time base (not shown in FIG. 3) coupled to processor 26 (such oscillators typically are quite stable). After reading the outputs of sensing elements 24, processor 26 performs an exclusive OR ("XOR") operation with the last data read (in a preferred embodiment such data is read in byte length). If any bit has changed, the XOR operation will produce a 1, and, if no bits have changed, the XOR operation will produce a 0. If the result is non-zero, the input byte is saved along with the value of the internal counter (that is incremented each pass through the software timing loop). If the result is zero, the systems waits (e.g., executes no operation instructions) the same amount of time as if the data had to be saved, and the looping operation continues. The process continues until all eight inputs have changed at least twice, which enables measurement of a full ½ period of each input. Upon conclusion of the looping process, processor 26 analyzes the stored input bytes and internal counter states. There should be 2 to 16 saved inputs (for the 8 total sensors of FIG. 3) and counter states (if two or more inputs change at the same time, they are saved simultaneously). As will be understood by one of skill in the art, the stored values of the internal counter contains information determinative of the period of the signals received from sensing elements 24. By proper subtraction of internal counter values at times when an input bit has changed, the period may be calculated. Such periods calculated for each of the outputs of sensing elements is provided by processor 26 to microprocessor 10 (see, e.g., FIG. 1). From such calculated periods, a measure of the received light intensities may be calculated.

It should be noted that the sensing circuitry and methodology illustrated in FIG. 3 have been determined to provide a practical and expedient manner in which to measure the light intensities received by sensing elements 24. In other embodiments, other circuits and methodologies are employed (other exemplary sensing schemes are described elsewhere herein).

As discussed above with reference to FIG. 1, one of fibers 7 measures light source 11, which may be through a neutral density filter, which serves to reduce the intensity of the received light in order maintain the intensity roughly in the range of the other received light intensities. Three of fibers 7 also are from perimeter receiver fiber optics R1 to R3 (see, e.g., FIG. 2) and also may pass through neutral density filters. Such receiving fibers 7 serve to provide data from which angle/height information and/or surface characteristics may be determined.

The remaining twelve fibers (of the preferred embodiment's total of 16 fibers) of fibers 7 pass through color filters and are used to produce the color measurement. In a preferred embodiment, the color filters are Kodak Sharp Cutting Wratten Gelatin Filters, which pass light with wavelengths greater than the cut-off value of the filter (i.e., redish values), and absorb light with wavelengths less than the cut-off value of the filter (i.e., bluish values). "Sharp Cutting" filters are available in a wide variety of cut-off frequencies/wavelengths, and the cut-off values generally may be selected by proper selection of the desired cut-off filter. In a preferred embodiment, the filter cut-off values are chosen to cover the entire visible spectrum and, in general, to have band spacings of approximately the visible band range (or other desired range) divided by the number of receivers/filters. As an example, 700 nanometers minus 400 nanometers, divided by 11 bands (produced by twelve color receivers/sensors), is roughly 30 nanometer band spacing.

With an array of cut-off filters as described above, and without being bound by theory or the specific embodiments described herein, the received optical spectrum may be measured/calculated by subtracting the light intensities of "adjacent" color receivers. For example, band 1 (400 nm to 430 nm)=(intensity of receiver 12) minus (intensity of receiver 11), and so on for the remaining bands. Such an array of cut-off filters, and the intensity values that may result from filtering with such an array, are more fully described in connection with FIGS. 13A to 14B.

In a preferred embodiment of the present invention, the specific characteristics of the light source, filters, sensors and fiber optics, etc., are normalized/calibrated by directing the probe towards, and measuring, a known color standard. Such normalization/calibration may be performed by placing the probe in a suitable fixture, with the probe directed from a predetermined position (i.e., height and angle) from the known color standard. Such measured normalization/calibration data may be stored, for example, in a look-up table, and used by microprocessor 10 to normalize or correct measured color or other data. Such procedures may be conducted at start-up, at regular periodic intervals, or by operator command, etc.

What should be noted from the above description is that the receiving and sensing fiber optics and circuitry illustrated in FIG. 3 provide a practical and expedient way to determine the intensity by color of the light reflected from the surface of the object being measured.

It also should be noted that such a system measures the spectral band of the reflected light from the object, and once measured such spectral data may be utilized in a variety of ways. For example, such spectral data may be displayed directly as intensity-wavelength band values. In addition, tristimulus type values may be readily computed (through, for example, conventional matrix math), or any other desired color values. In one particular embodiment useful in dental applications (such as for dental prostheses), the color data is output in the form of a closest match or matches of dental shade guide value(s). In a preferred embodiment, various existing shade guides (such as the shade guides produced by Vita Zahnfabrik) are characterized and stored in a look-up table, and the color measurement data are used to select the closest shade guide value. In still other embodiments, the color measurement data are used (such as with look-up tables) to select materials for the composition of paint or ceramics such as for prosthetic teeth. There are many other uses of such spectral data measured in accordance with the present invention.

It is known that certain objects such as human teeth may fluoresce, and such characteristics also may be measured in accordance with the present invention. A light source with an ultraviolet component may be used to produce more accurate color data of such objects. In certain embodiments, a tungsten/halogen source (such as used in a preferred embodiment) may be combined with a UV light source (such as a mercury vapor, xenon or other fluorescent light source, etc.) to produce a light output capable of causing the object to fluoresce. Alternately, a separate UV light source, combined with a visible-light-blocking filter, may be used to illuminate the object. Such a UV light source may be combined with light from a red LED (for example) in order to provide a visual indication of when the UV light is on and also to serve as an aid for the directional positioning of the probe operating with such a light source. A second measurement may be taken using the UV light source in a manner analogous to that described earlier, with the band of the red LED or other supplemental light source being ignored. The second measurement may thus be used to produce an indication of the fluorescence of the tooth or other object being measured. With such a UV light source, a silica fiber optic (or other suitable material) typically would be required to transmit the light to the object (standard fiber optic materials such as glass and plastic do not propagate UV light in a desired manner, etc.).

As described earlier, the present invention utilizes a plurality of perimeter receiver fiber optics spaced apart from and around a central source fiber optic to measure color and determine information regarding the height and angle of the probe with respect to the surface of the object being measured, which may include surface characteristic information, etc. Without being bound by theory, a principle underlying this aspect of the present invention will now be described with reference to FIGS. 4A to 4C.

Figure 4A:
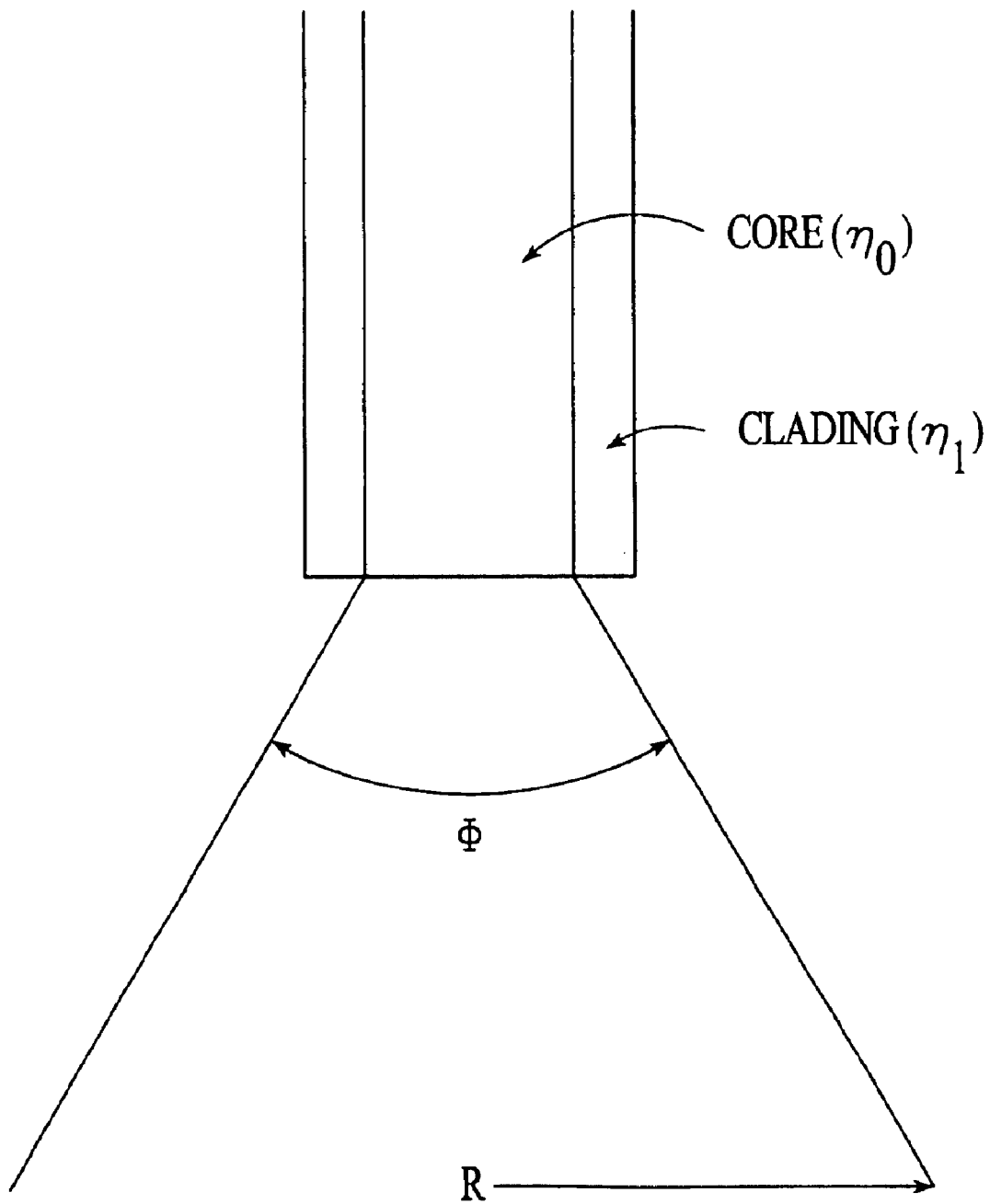
FIGS. 4A to 4C illustrate certain geometric considerations of fiber optics.

FIG. 4A illustrates a typical step index fiber optic consisting of a core and a cladding. For this discussion, it is assumed that the core has an index of refraction of $n_0$ and the cladding has an index of refraction of $n_1$. Although the following discussion is directed to "step index" fibers, it will be appreciated by those of skill in the art that such discussion generally is applicable for gradient index fibers as well.

In order to propagate light without loss, the light must be incident within the core of the fiber optic at an angle less than the critical angle, phi, where phi=$Sin^{-1}\{n_1/n_0\}$, where $n_0$ is the index of refraction of the core and $n_1$ is the index of refraction of the cladding. Thus, all light must enter the fiber at an angle less than the critical angle, or it will not be propagated in a desired manner.

For light entering a fiber optic, it must enter within the acceptance angle phi. Similarly, when the light exits a fiber optic, it will exit the fiber optic within a cone of angle phi as illustrated in FIG. 4A. The ratio of the index of refraction of the cladding and core ($n_1/n_0$) is referred to as the aperture of the fiber optic. Typical fiber optics have an aperture of 0.5, and thus an acceptance/critical angle of 60°.

Consider using a fiber optic as a light source. One end is illuminated by a light source (such as light source 11 of FIG. 1), and the other is held near a surface. The fiber optic will emit a cone of light as illustrated in FIG. 4A. If the fiber optic is held perpendicular to a surface it will create a circular light pattern on the surface. As the fiber optic is raised, the radius r of the circle will increase. As the fiber optic is lowered, the radius of the light pattern will decrease. Thus, the intensity of the light (light energy per unit area) in the illuminated circular area will increase as the fiber optic is lowered and will decrease as the fiber optic is raised.

The same principle generally is true for a fiber optic being utilized as a receiver. Consider mounting a light sensor on one end of a fiber optic and holding the other end near an illuminated surface. The fiber optic can only propagate light without loss when the light entering the fiber optic is incident on the end of the fiber optic near the surface if the light enters the fiber optic within its acceptance angle phi. A fiber optic utilized as a light receiver near a surface will only accept and propagate light from the circular area of radius r on the surface. As the fiber optic is raised from the surface, the area increases. As the fiber optic is lowered to the surface, the area decreases.

Figure 4B:
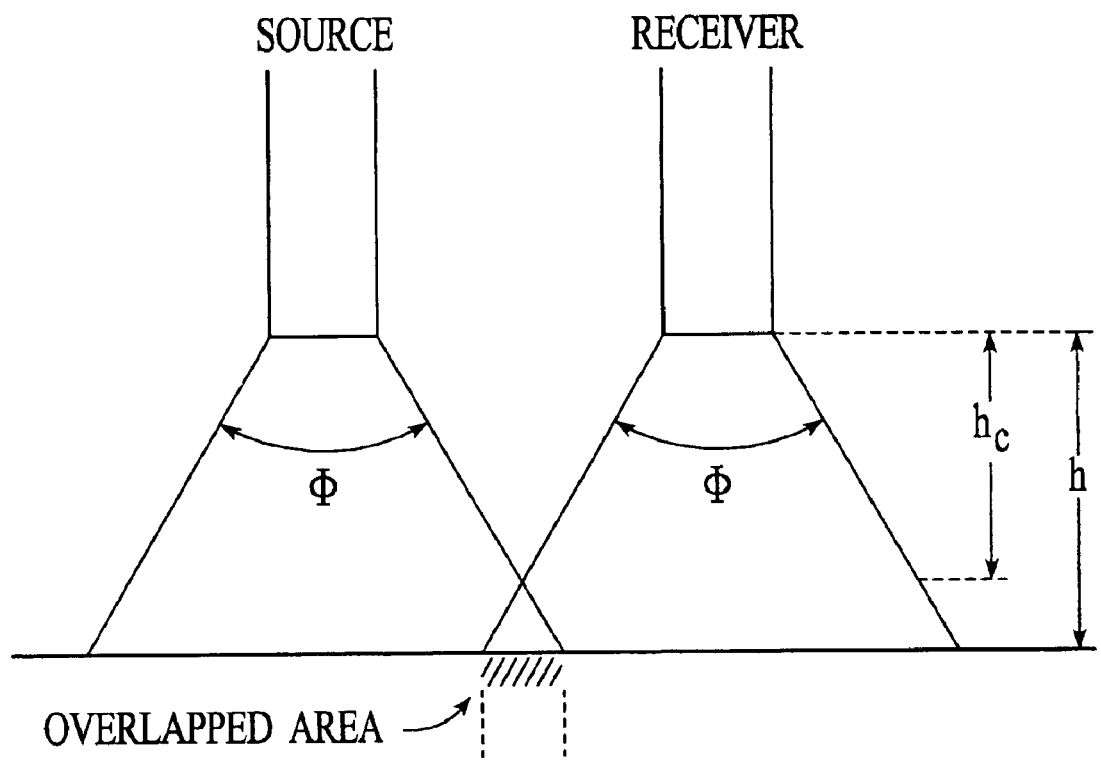
Figure 4C:
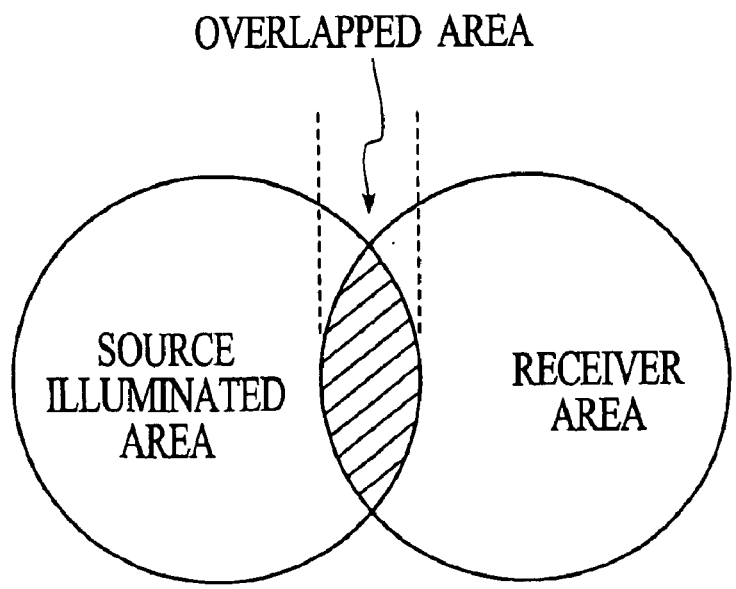

Consider two fiber optics parallel to each other as illustrated in FIG. 4B. For simplicity of discussion, the two fiber optics illustrated are identical in size and aperture. The following discussion, however, generally would be applicable for fiber optics that differ in size and aperture. One fiber optic is a source fiber optic, the other fiber optic is a receiver fiber optic. As the two fiber optics are held perpendicular to a surface, the source fiber optic emits a cone of light that illuminates a circular area of radius r. The receiver fiber optic can only accept light that is within its acceptance angle phi, or only light that is received within a cone of angle phi. If the only light available is that emitted by the source fiber optic, then the only light that can be accepted by the receiver fiber optic is the light that strikes the surface at the intersection of the two circles as illustrated in FIG. 4C. As the two fiber optics are lifted from the surface, the proportion of the intersection of the two circular areas relative to the circular area of the source fiber optic increases. As they near the surface, the proportion of the intersection of the two circular areas to the circular area of the source fiber optic decreases. If the fiber optics are held too close to the surface, the circular areas will no longer intersect and no light emitted from the source fiber optic will be received by the receiver fiber optic.

As discussed earlier, the intensity of the light in the circular area illuminated by the source fiber increases as the fiber is lowered to the surface. The intersection of the two cones, however, decreases as the fiber optic pair is lowered. Thus, as the fiber optic pair is lowered to a surface, the total intensity of light received by the receiver fiber optic increases to a maximal value, and then decreases sharply is the fiber optic pair is lowered still further to the surface. Eventually, the intensity will decrease essentially to zero (assuming the object being measured is not translucent, as described more fully herein), and will remain essentially zero until the fiber optic pair is in contact with the surface. Thus, as a source-receiver pair of fiber optics as described above are positioned near a surface and as their height is varied, the intensity of light received by the receiver fiber optic reaches a maximal value at a critical height $h_c$.

Again without being bound by theory, an interesting property of the critical height $h_c$ has been observed. The critical height $h_c$ is a function primarily of the geometry of fixed parameters, such as fiber apertures, fiber diameters and fiber spacing. Since the receiver fiber optic in the illustrated arrangement is only detecting a maximum value and not attempting to quantify the value, its maximum is independent of the surface characteristics. It is only necessary that the surface reflect sufficient light from the intersecting area of the source and receiver fiber optics to be within the detection range of the receiver fiber optic light sensor. Thus, red or green or blue or any color surface will all exhibit a maximum at the same critical height $h_c$. Similarly, smooth reflecting surfaces and rough surfaces also will have varying intensity values at the maximal value, but generally speaking all such surfaces will exhibit a maximum at the same critical height $h_c$. The actual value of the light intensity will be a function of the color of the surface and of the surface characteristics, but the height where the maximum intensity value occurs in general will not.

Although the above discussion has focused on two fiber optics perpendicular to a surface, similar analysis is applicable for fiber optic pairs at other angles. When a fiber optic is not perpendicular to a surface, it generally illuminates an elliptical area. Similarly, the acceptance area of a receiver fiber optic generally becomes elliptical. As the fiber optic pair is moved closer to the surface, the receiver fiber optic also will detect a maximal value at a critical height independent of the surface color or characteristics. The maximal intensity value measured when the fiber optic pair is not perpendicular to the surface, however, will be less than the maximal intensity value measured when the fiber optic pair is perpendicular to the surface.

Figure 5A:
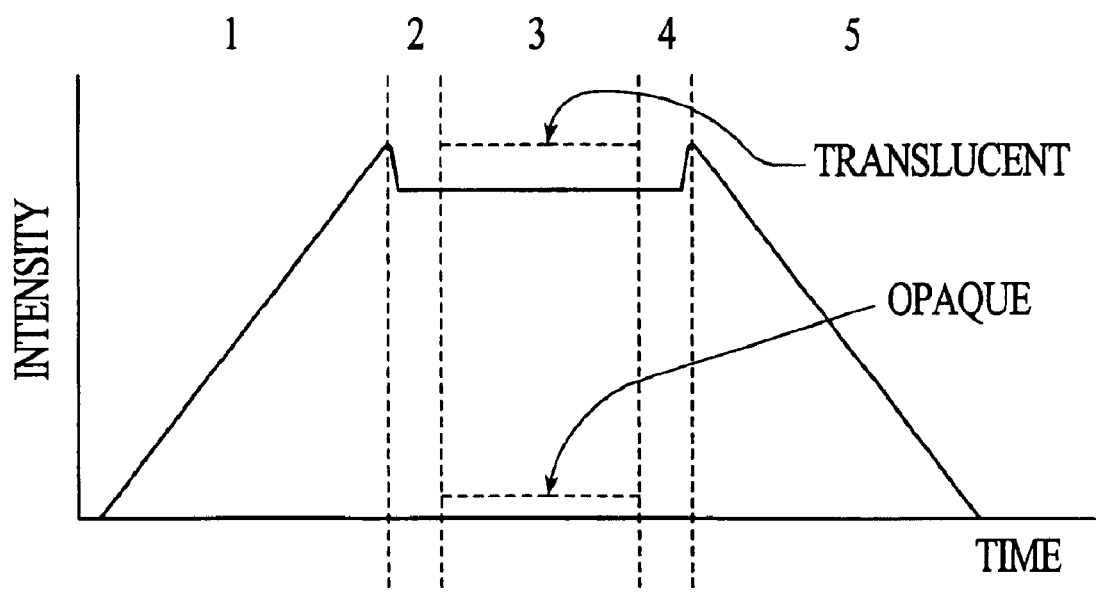
FIGS. 5A and 5B illustrate the light amplitude received by fiber optic light receivers as a function of height from an object.
Figure 5B:
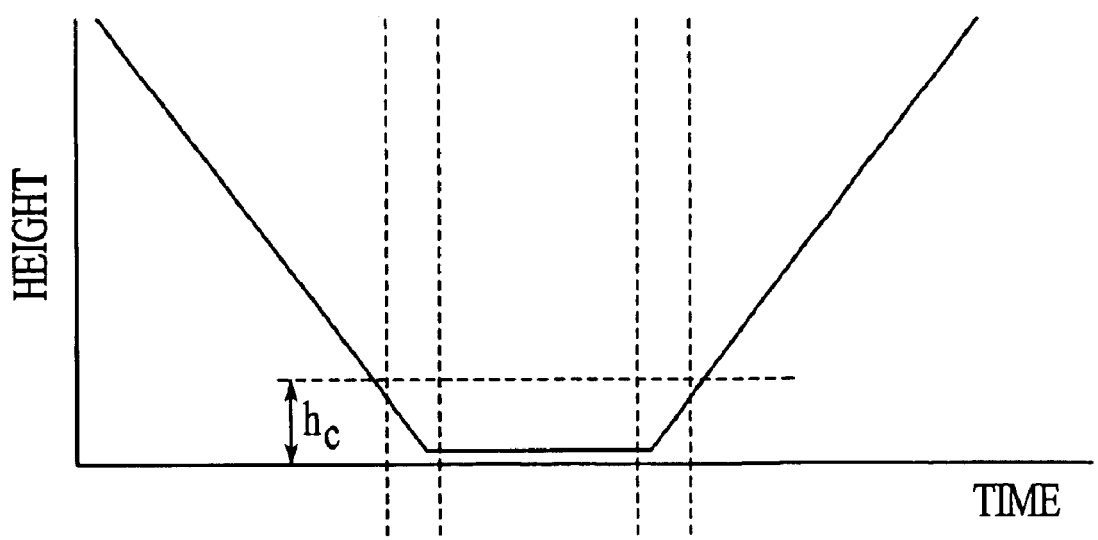

Referring now to FIGS. 5A and 5B, the intensity of light received as a fiber optic source-receiver pair is moved to and from a surface will now be described. FIG. 5A illustrates the intensity of the received light as a function of time. Corresponding FIG. 5B illustrates the height of the fiber optic pair from the surface of the object being measured. FIGS. 5A and 5B illustrate (for ease of discussion) a relatively uniform rate of motion of the fiber optic pair to and from the surface of the object being measured (although similar illustrations/analysis would be applicable for non-uniform rates as well).

FIG. 5A illustrates the intensity of received light as the fiber optic pair is moved to and then from a surface. While FIG. 5A illustrates the intensity relationship for a single receiver fiber optic, similar intensity relationships would be expected to be observed for other receiver fiber optics, such as, for example, the multiple receiver fiber optics of FIGS. 1 and 2. In general with the preferred embodiment described above, all fifteen fiber optic receivers (of fibers 7) will exhibit curves similar to that illustrated in FIG. 5A.

FIG. 5A illustrates five regions. In region 1, the probe is moved towards the surface of the object being measured, which causes the received light intensity to increase. In region 2, the probe is moved past the critical height, and the received light intensity peaks and then falls off sharply. In region 3, the probe essentially is in contact with the surface of the object being measured. As illustrated, the received intensity in region 3 will vary depending upon the translucence of the object being measured. If the object is opaque, the received light intensity will be very low, or almost zero (perhaps out of range of the sensing circuitry). If the object is translucent, however, the light intensity will be quite high, but in general should be less than the peak value. In region 4, the probe is lifted and the light intensity rises sharply to a maximum value. In region 5, the probe is lifted further away from the object, and the light intensity decreases again.

As illustrated, two peak intensity values (discussed as P1 and P2 below) should be detected as the fiber optic pair moves to and from the object at the critical height $h_c$. If peaks P1 and P2 produced by a receive fiber optic are the same value, this generally is an indication that the probe has been moved to and from the surface of the object to be measured in a consistent manner. If peaks P1 and P2 ire of different values, then these may be an indication that the probe was not moved to and from the surface of the object in a desired manner, or that the surface is curved or textured, as described more fully herein. In such a case, the data may be considered suspect and rejected. In addition, peaks P1 and P2 for each of the perimeter fiber optics (see, e.g., FIG. 2) should occur at the same critical height (assuming the geometric attributes of the perimeter fiber optics, such as aperture, diameter and spacing from the source fiber optic, etc.). Thus, the perimeter fiber optics of a probe moved in a consistent, perpendicular manner to and from the surface of the object being measured should have peaks P1 and P2 that occur at the same critical height. Monitoring receiver fibers from the perimeter receiver fiber optics and looking for simultaneous (or near simultaneous, e.g., within a predetermined range) peaks P1 and P2 provides a mechanism for determining if the probe is held at a desired perpendicular angle with respect to the object being measured.

In addition, the relative intensity level in region 3 serves as an indication of the level of translucency of the object being measured. Again, such principles generally are applicable to the totality of receiver fiber optics in the probe (see, e.g., fibers 7 of FIGS. 1 and 3). Based on such principles, measurement techniques in accordance with the present invention will now be described.

Figure 6:
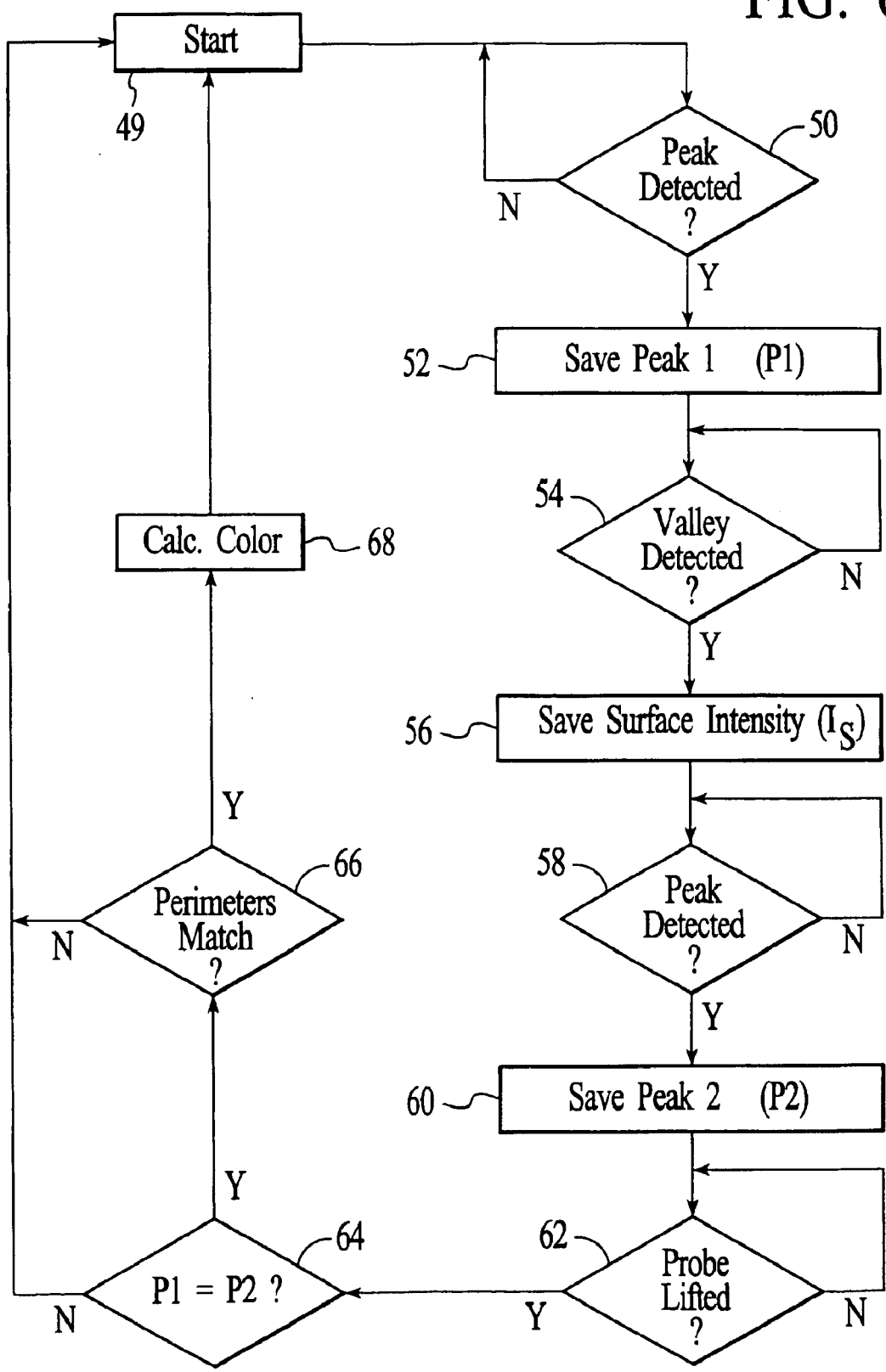
FIG. 6 is a flow chart illustrating a color measuring method in accordance with an embodiment of the present invention.

FIG. 6 is a flow chart illustrating a measuring technique in accordance with the present invention. Step 49 indicates the start or beginning of a color measurement. During step 49, any equipment initialization, diagnostic or setup procedures may be performed. Audio or visual information or other indicia may be given to the operator to inform the operator that the system is available and ready to take a measurement. Initiation of the color measurement commences by the operator moving the probe towards the object to be measured, and may be accompanied by, for example, activation of switch 17 (see FIG. 1).

In step 50, the system on a continuing basis monitors the intensity levels for the receiver fiber optics (see, e.g., fibers 7 of FIG. 1). If the intensity is rising, step 50 is repeated until a peak is detected. If a peak is detected, the process proceeds to step 52. In step 52, measured peak intensity P1, and the time at which such peak occurred, are stored in memory (such as in memory included as a part of microprocessor 10), and the process proceeds to step 54. In step 54, the system continues to monitor the intensity levels of the receiver fiber optics. If the intensity is falling, step 54 is repeated. If a "valley" or plateau is detected (i.e., the intensity is no longer falling, which generally indicates contact or near contact with the object), then the process proceeds to step 56. In step 56, the measured surface intensity (IS) is stored in memory, and the process proceeds to step 58. In step 58, the system continues to monitor the intensity levels of the receiver fibers. If the intensity is rising, step 58 is repeated until a peak is detected. If a peak is detected, the process proceeds to step 60. In step 60, measured peak intensity P2, and the time at which such peak occurred, are stored in memory, and the process proceeds to step 62. In step 62, the system continues to monitor the intensity levels of the receiver fiber optics. Once the received intensity levels begin to fall from peak P2, the system perceives that region 5 has been entered (see, e.g., FIG. 5A), and the process proceeds to step 64.

In step 64, the system, under control of microprocessor 10, may analyze the collected data taken by the sensing circuitry for the various receiver fiber optics. In step 64, peaks P1 and P2 of one or more of the various fiber optics may be compared. If any of peaks P1 and P2 for any of the various receiver fiber optics have unequal peak values, then the color data may be rejected, and the entire color measuring process repeated. Again, unequal values of peaks P1 and P2 may be indicative, for example, that the probe was moved in a non-perpendicular or otherwise unstable manner (i.e., angular or lateral movement), and, for example, peak P1 may be representative of a first point on the object, while peak P2 may be representative of a second point on the object. As the data is suspect, in a preferred embodiment of the present invention, color data taken in such circumstances are rejected in step 64.

If the data are not rejected in step 64, the process proceeds to step 66. In step 66, the system analyzes the data taken from the neutral-density-filtered receivers from each of the perimeter fiber optics (e.g., R1 to R3 of FIG. 2). If the peaks of the perimeter fiber optics did not occur at or about the same point in time, this may be indicative, for example, that the probe was not held perpendicular to the surface of the object being measured. As non-perpendicular alignment of the probe with the surface of the object being measured may cause suspect results, in a preferred embodiment of the present invention, color data taken in such circumstances are rejected in step 66. In one preferred embodiment, detection of simultaneous or near simultaneous peaking (peaking within a predetermined range of time) serves as an acceptance criterion for the data, as perpendicular alignment generally is indicated by simultaneous or near simultaneous peaking of the perimeter fiber optics. In other embodiments, step 66 includes an analysis of peak values P1 and P2 of the perimeter fiber optics. In such embodiments, the system seeks to determine if the peak values of the perimeter fiber optics (perhaps normalized with any initial calibration data) are equal within a defined range. If the peak values of the perimeter fiber optics are within the defined range, the data may be accepted, and if not, the data may be rejected. In still other embodiments, a combination of simultaneous peaking and equal value detection are used as acceptance/rejection criteria for the color data, and/or the operator may have the ability (such as through key pad switches 12) to control one or more of the acceptance criteria ranges. With such capability, the sensitivity of the system may be controllably altered by the operator depending upon the particular application and operative environment, etc.

If the data are not rejected in step 66, the process proceeds to step 68. In step 68, the color data may be processed in a desired manner to produce output color measurement data. For example, such data may be normalized in some manner, or adjusted based on temperature compensation or other data detected by the system. The data also may be converted to different display or other formats, depending on the intended use of the color data. In addition, the data indicative of the translucence of the object also may be quantified and/or displayed in step 68. After step 68, the process may proceed to starting step 49, or the process may be terminated, etc.

In accordance the process illustrated in FIG. 6, three light intensity values (P1, P2 and PS) are stored per receiver fiber optic to make color and translucency measurements. If stored peak values P1 and P2 are not equal (for some or all of the receivers), this is an indication that the probe was not held steady over one area, and the data may be rejected (in other embodiments, the data may not be rejected, although the resulting data may be used to produce an average of the measured color data). In addition, peak values P1 and P2 for the three neutral density perimeter fiber optics should be equal or approximately equal; if this is not the case, then this is an indication that the probe was not held perpendicular or a curved surface is being measured. In other embodiments, the system attempts to compensate for curved surfaces and/or non-perpendicular angles. In any event, if the system cannot make a color measurement, or if the data is rejected because peak values P1 and P2 are unequal to an unacceptable degree, then the operator is notified so that another measurement or other action may be taken (such as adjust the sensitivity).

With a system constructed and operating as described above, color measurements may be taken of an object, with accepted color data having height and angular dependencies removed. Data not taken at the critical height, or data not taken with the probe perpendicular to the surface of the object being measured, etc., are rejected in a preferred embodiment of the present invention. In other embodiments, data received from the perimeter fiber optics may be used to calculate the angle of the probe with respect to the surface of the object being measured, and in such embodiments non-perpendicular or curved surface color data may be compensated instead of rejected. It also should be noted that peak values P1 and P2 for the neutral density perimeter fiber optics provide a measure of the luminance (gray value) of the surface of the object being measured, and also may serve to quantify the color value.

The translucency of the object being measured may be quantified as a ratio or percentage, such as, for example, (IS/P1)×100%. In other embodiments, other methods of quantifying translucency data provided in accordance with the present invention are utilized.

In another particular aspect of the present invention, data generated in accordance with the present invention may be used to implement an automated material mixing/generation machine. Certain objects/materials, such as dental prostheses, are made from porcelain or other powders/ materials that may be combined in the correct ratios to form the desired color of the object/prosthesis. Certain powders often contain pigments that generally obey Beer's law and/or act in accordance with Kubelka-Munk equations when mixed in a recipe. Color and other data taken from a measurement in accordance with the present invention may be used to determine or predict desired quantities of pigment or other materials for the recipe. Porcelain powders and other materials are available in different colors, opacities, etc. Certain objects, such as dental prostheses, may be layered to simulate the degree of translucency of the desired object (such as to simulate a human tooth). Data generated in accordance with the present invention also may be used to determine the thickness and position of the porcelain or other material layers to more closely produce the desired color, translucency, surface characteristics, etc. In addition, based on fluorescence data for the desired object, the material recipe may be adjusted to include a desired quantity of fluorescing-type material. In yet other embodiments, surface characteristics (such as texture) information (as more fully described herein) may be used to add a texturing material to the recipe, all of which may be carried out in accordance with the present invention.

For more information regarding such pigment-material recipe type technology, reference may be made to: "The Measurement of Appearance," Second Edition, edited by Hunter and Harold, copyright 1987; "Principles of Color Technology," by Billmeyer and Saltzman, copyright 1981; and "Pigment Handbook," edited by Lewis, copyright 1988. All of the foregoing are believed to have been published by John Wiley & Sons, Inc., New York, N.Y., and all of which are hereby incorporated by reference.

In certain operative environments, such as dental applications, contamination of the probe is of concern. In certain embodiments of the present invention, implements to reduce such contamination are provided.

Figure 7A:
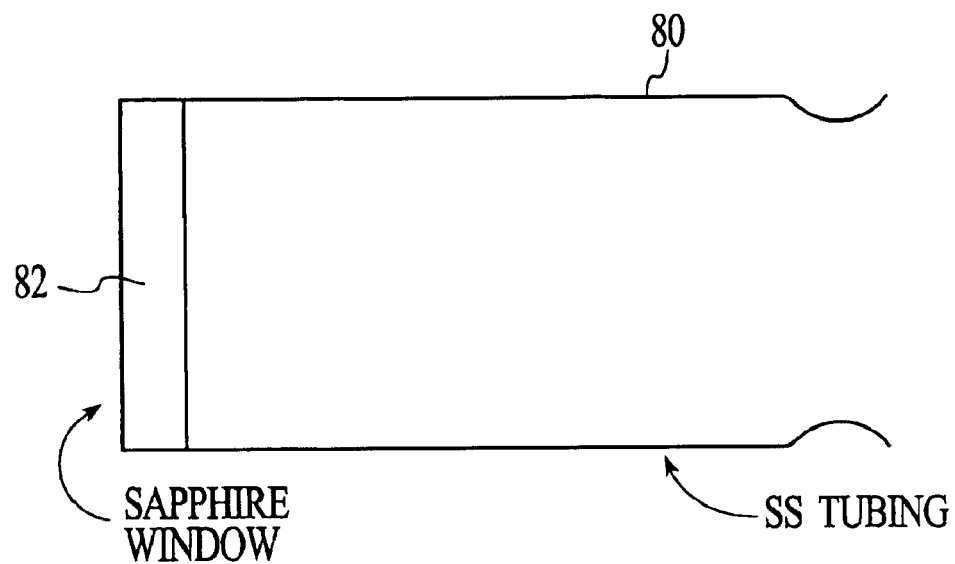
FIGS. 7A and 7B illustrate a protective cap that may be used with certain embodiments of the present invention.
Figure 7B:
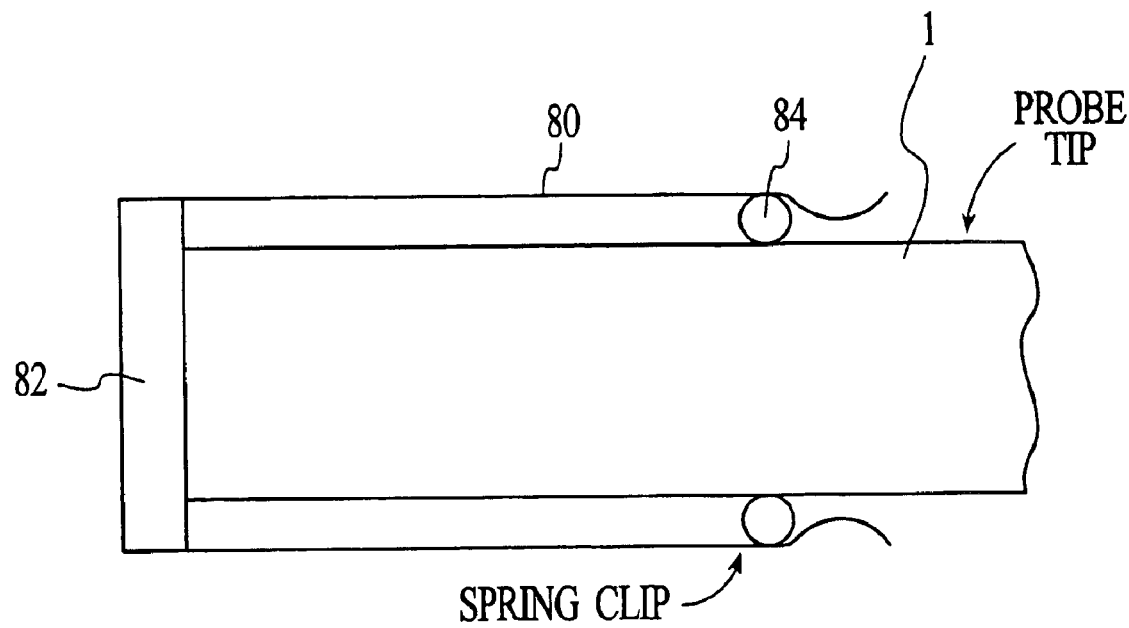

FIGS. 7A and 7B illustrate a protective cap that may be used to fit over the end of probe tip 1. Such a protective cap consists of body 80, the end of which is covered by optical window 82, which in a preferred embodiment consists of a structure having a thin sapphire window. In a preferred embodiment, body 80 consists of stainless steel. Body 80 fits over the end of probe tip 1 and may be held into place by, for example, indentations formed in body 80, which fit with ribs 84 (which may be a spring clip or other retainer) formed on probe tip 1. In other embodiments, other methods of affixing such a protective cap to probe tip 1 are utilized. The protective cap may be removed from probe tip 1 and sterilized in a typical autoclave, hot steam or other sterilizing system.

The thickness of the sapphire window should be less than the critical height of the probe in order to preserve the ability to detect peaking in accordance with the present invention. It also is believed that sapphire windows may be manufactured in a reproducible manner, and thus any light attenuation from one cap to another may be reproducible. In addition, any distortion of the color measurements produced by the sapphire window may be calibrated out by microprocessor 10.

Similarly, in other embodiments body 80 has a cap with a hole in the center (as opposed to a sapphire window), with the hole positioned over the fiber optic source/receivers. The cap with the hole serves to prevent the probe from coming into contact with the surface, thereby reducing the risk of contamination.

Figure 8A:
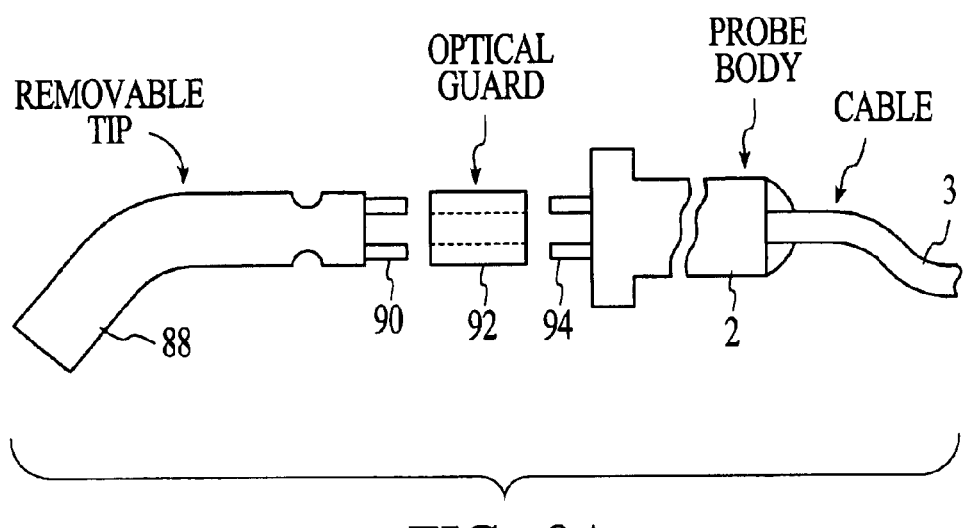
FIGS. 8A and 8B illustrate removable probe tips that may be used with certain embodiments of the present invention.
Figure 8B:
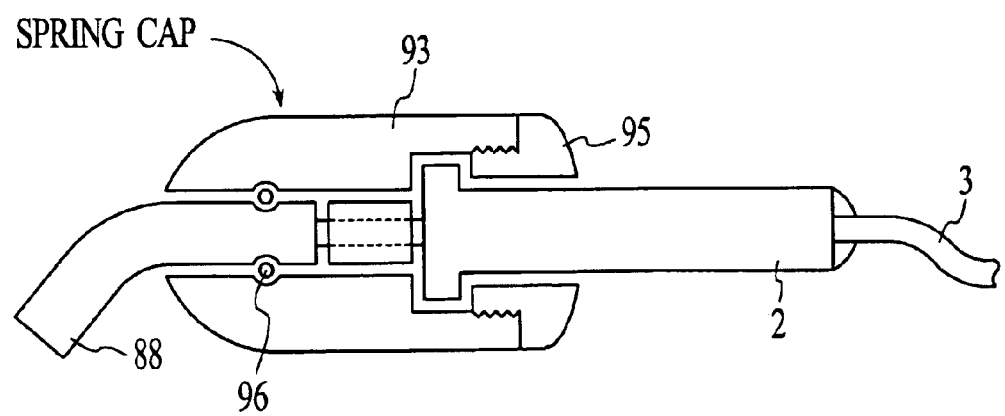

FIGS. 8A and 8B illustrate another embodiment of a removable probe tip that may be used to reduce contamination in accordance with the present invention. As illustrated in FIG. 8A, probe tip 88 is removable, and includes four (or a different number, depending upon the application) fiber optic connectors 90, which are positioned within optical guard 92. Optical guard 92 serves to prevent "cross talk" between adjacent fiber optics. As illustrated in FIG. 8B, in this embodiment removable tip 88 is secured in probe tip housing 92 by way of spring clip 96 (other removable retaining implements are utilized in other embodiments). Probe tip housing 92 may be secured to base connector 94 by a screw or other conventional fitting. It should be noted that, with this embodiment, different size tips may be provided for different applications, and that an initial step of the process may be to install the properly-sized (or fitted tip) for the particular application. Removable tip 88 also may be sterilized in a typical autoclave, hot steam or other sterilizing system. In addition, the entire probe tip assembly is constructed so that it may be readily disassembled for cleaning or repair.

Figure 9:
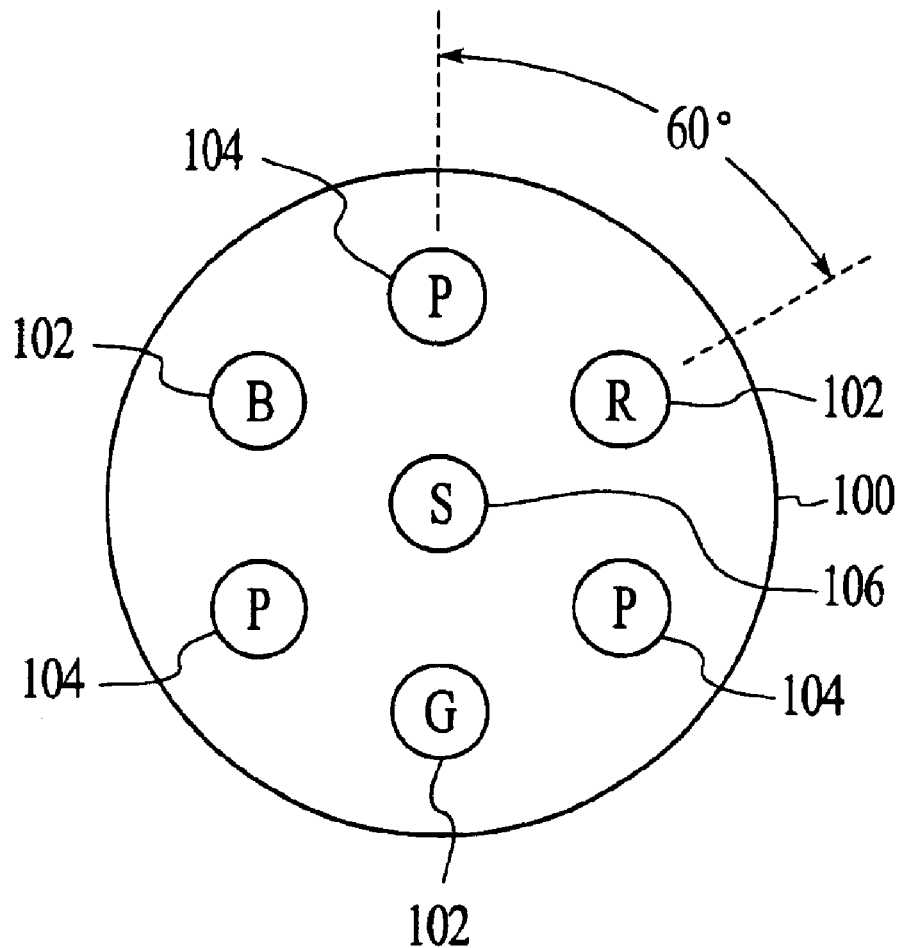
FIG. 9 illustrates a fiber optic bundle in accordance with another preferred embodiment of the present invention.

With reference to FIG. 9, a tristimulus embodiment of the present invention will now be described. In general, the overall system depicted in FIG. 1 and discussed in detail elsewhere herein may be used with this embodiment. FIG. 9 illustrates a cross section of the probe tip fiber optics used in this embodiment.

Probe tip 100 includes central source fiber optic 106, surrounded by (and spaced apart from) three perimeter receiver fiber optics 104 and three color receiver fiber optics 102. Three perimeter receiver fiber optics 104 are optically coupled to neutral density filters and serve as height/angle sensors in a manner analogous to the embodiment describe above. Three color receiver fiber optics are optically coupled to suitable tristimulus filters, such as red, green and blue filters. With this embodiment, a measurement may be made of tristimulus color values of the object, and the process described with reference to FIG. 6 generally is applicable to this embodiment. In particular, perimeter fiber optics 104 may be used to detect simultaneous peaking or otherwise whether the probe is perpendicular to the object being measured. In addition, taking color measurement data at the critical height also may be used with this embodiment.

Figure 10A:
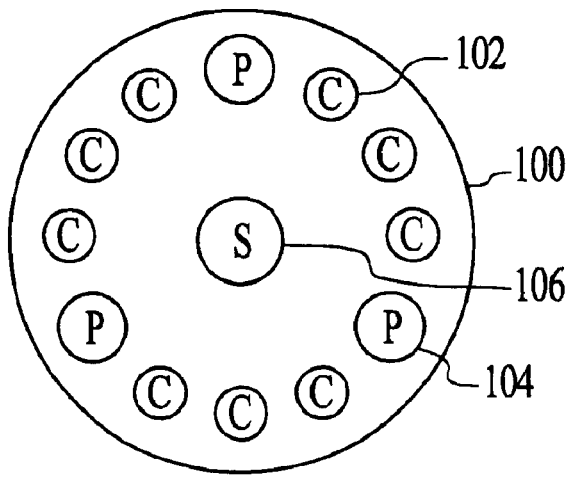
FIGS. 10A, 10B, 10C and 10D illustrate and describe other fiber optic bundle configurations that may be used in accordance with yet other preferred embodiments of the present invention.

FIG. 10A illustrates an embodiment of the present invention, similar to the embodiment discussed with reference to FIG. 9. Probe tip 100 includes central source fiber optic 106, surrounded by (and spaced apart from) three perimeter receiver fiber optics 104 and a plurality of color receiver fiber optics 102. The number of color receiver fiber optics 102, and the filters associated with such receiver fiber optics 102, may be chosen based upon the particular application. As with the embodiment of FIG. 9, the process described with reference to FIG. 6 generally is applicable to this embodiment.

Figure 10B:
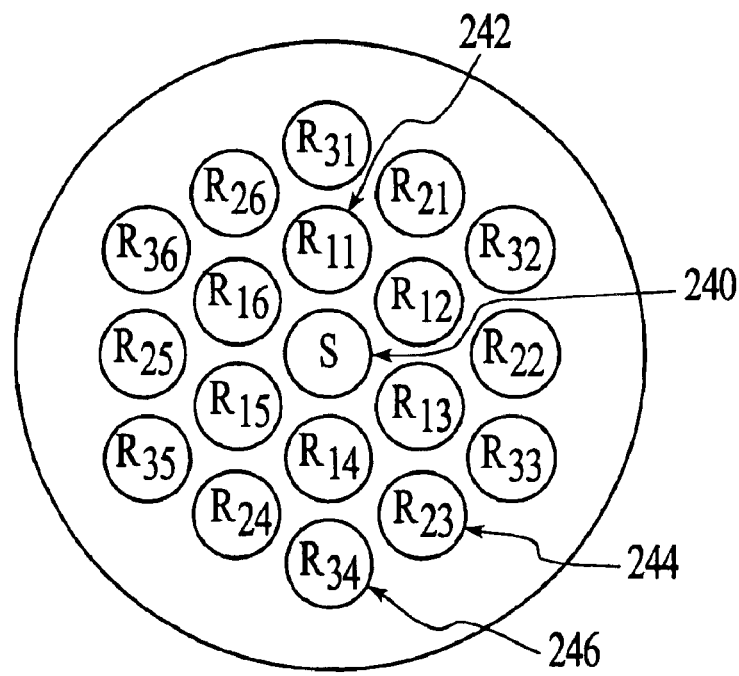

FIG. 10B illustrates an embodiment of the present invention in which there are a plurality of receiver fiber optics that surround central source fiber optic 240. The receiver fiber optics are arranged in rings surrounding the central source fiber optic. FIG. 10B illustrates three rings of receiver fiber optics (consisting of fiber optics 242, 244 and 246, respectively), in which there are six receiver fiber optics per ring. The rings may be arranged in successive larger circles as illustrated to cover the entire area of the end of the probe, with the distance from each receiver fiber optic within a given ring to the central fiber optic being equal (or approximately so). Central fiber optic 240 is utilized as the light source fiber optic and is connected to the light source in a manner similar to light source fiber optic 5 illustrated in FIG. 1.

The plurality of receiver fiber optics are each coupled to two or more fiber optics in a manner similar to the arrangement illustrated in FIG. 1 for splicing connector 4. One fiber optic from such a splicing connector for each receiver fiber optic passes through a neutral density filter and then to light sensor circuitry similar to the light sensor circuitry illustrated in FIG. 3. A second fiber optic from the splicing connector per receiver fiber optic passes through a Sharp Cutting Wrattan Gelatin Filter and then to light sensor circuitry as discussed elsewhere herein. Thus, each of the receiver fiber optics in the probe tip includes both color measuring elements and neutral light measuring or "perimeter" elements.

Figure 10C:
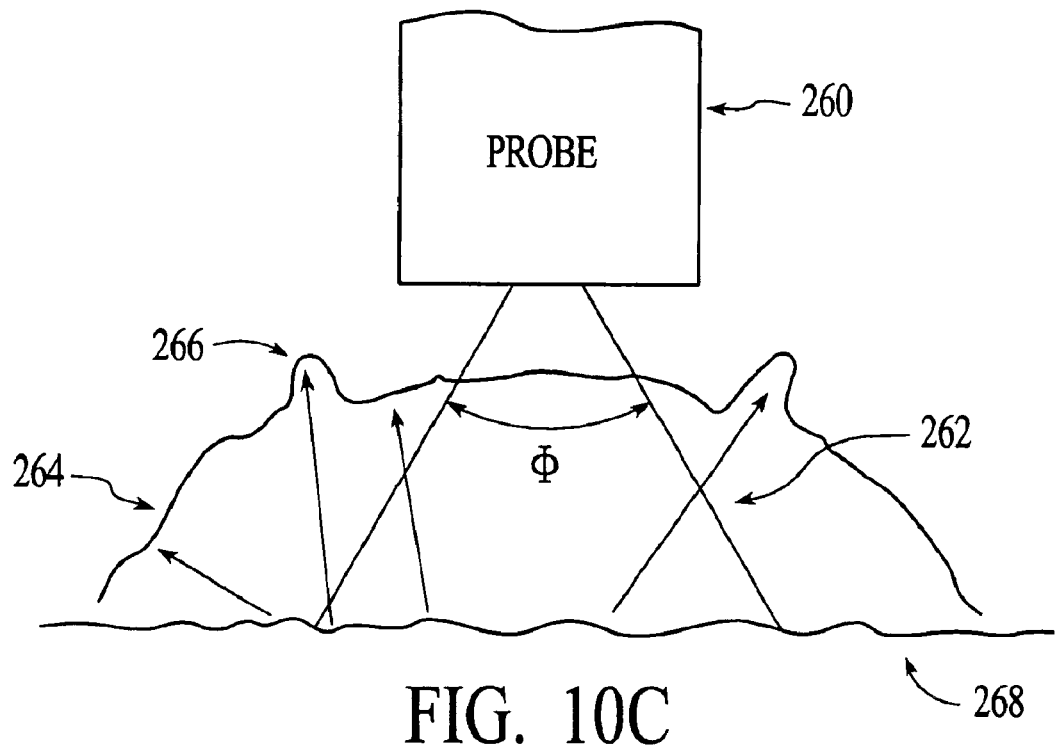
Figure 10D:
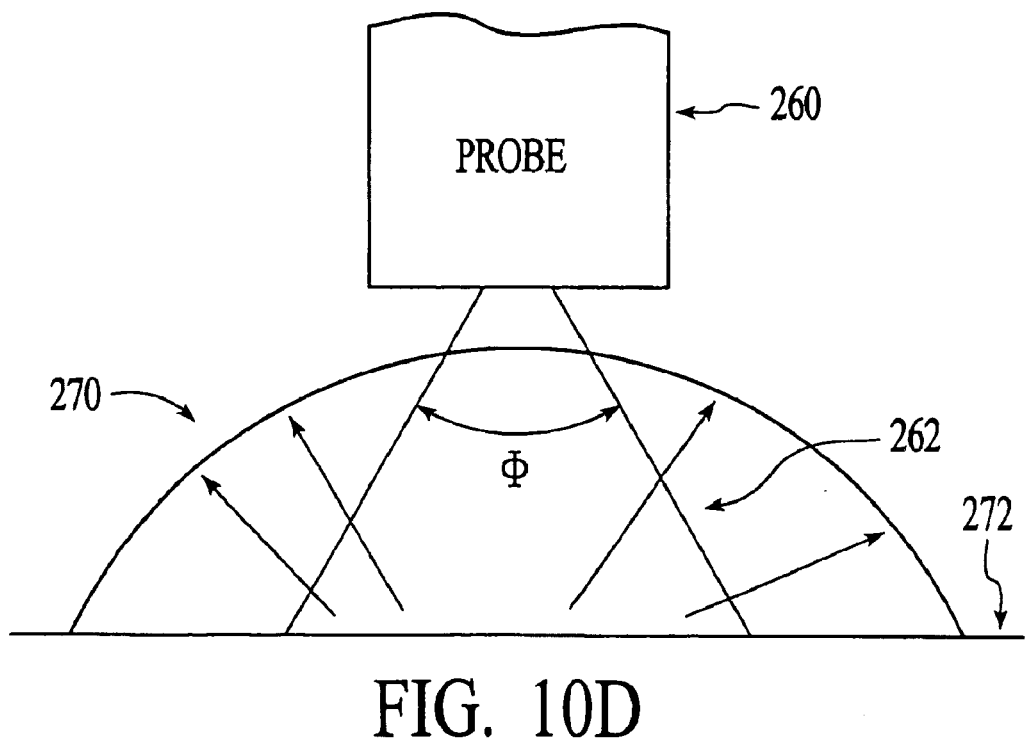

FIG. 10D illustrates the geometry of probe 260 (such as described above) illuminating an area on flat diffuse surface 272. Probe 260 creates light pattern 262 that is reflected diffusely from surface 272 in uniform hemispherical pattern 270. With such a reflection pattern, the reflected light that is incident upon the receiving elements in the probe will be equal (or nearly equal) for all elements if the probe is perpendicular to the surface as described above herein.

FIG. 10C illustrates a probe illuminating rough surface 268 or a surface that reflects light spectrally. Spectral reflected light will exhibit hot spots or regions where the reflected light intensity is considerably greater than it is on other areas. The reflected light pattern will be uneven when compared to a smooth surface as illustrate in FIG. 10D.

Since a probe as illustrated in FIG. 10B has a plurality of receiver fiber optics arranged over a large surface area, the probe may be utilized to determine the surface texture of the surface as well as being able to measure the color and translucency of the surface as described earlier herein. If the light intensity received by the receiver fiber optics is equal for all fiber optics within a given ring of receiver fiber optics, then generally the surface is diffuse and smooth. If, however, the light intensity of receiver fibers in a ring varies with respect to each other, then generally the surface is rough or spectral. By comparing the light intensities measured within receiver fiber optics in a given ring and from ring to ring, the texture and other characteristics of the surface may be quantified.

Figure 11:
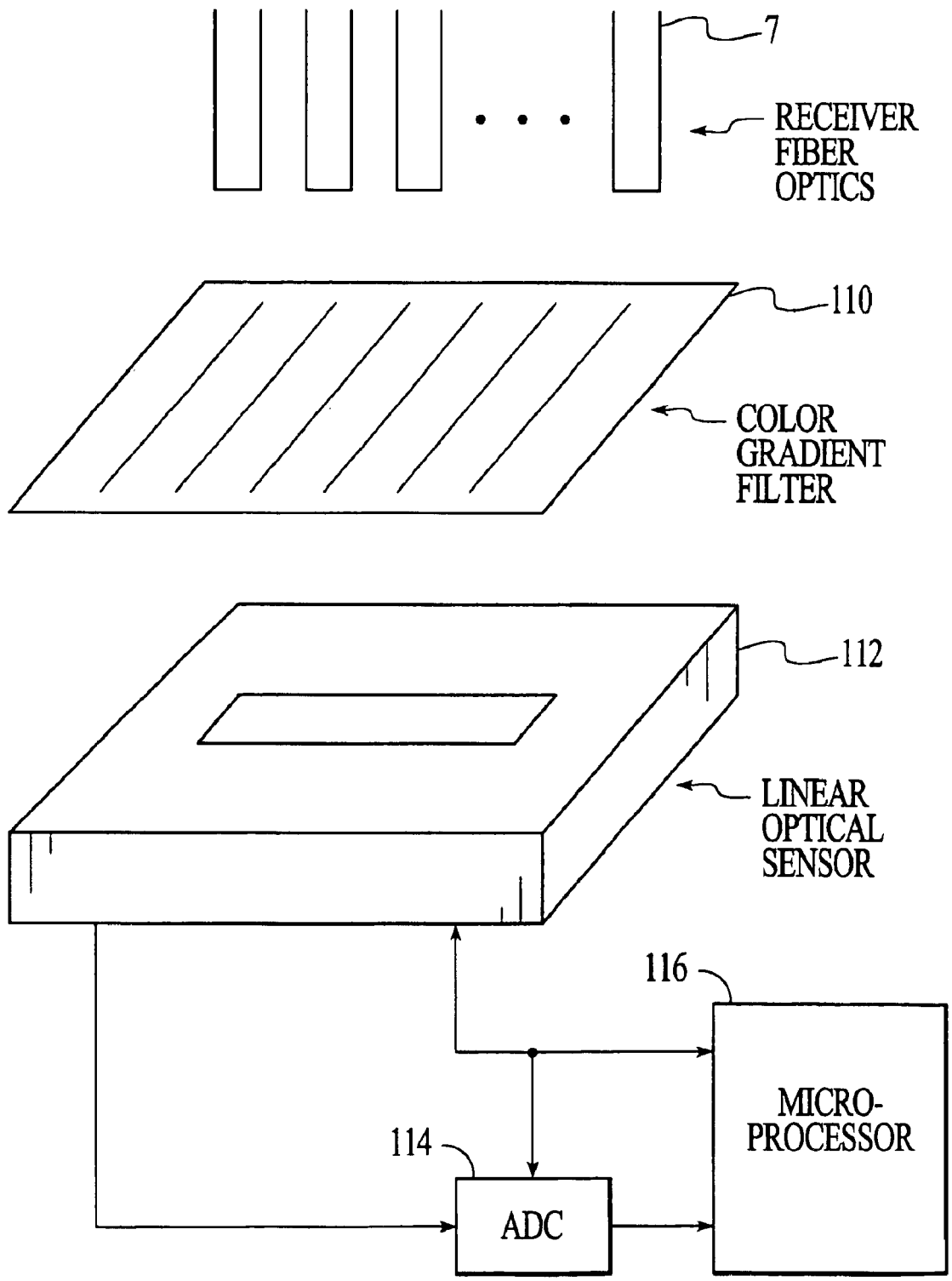
FIG. 11 illustrates a linear optical sensor array that may be used in certain embodiments of the present invention.

FIG. 11 illustrates an embodiment of the present invention in which linear optical sensors and a color gradient filter are utilized instead of light sensors 8 (and filters 22, etc.). Receiver fiber optics 7, which may be optically coupled to probe tip 1 as with the embodiment of FIG. 1, are optically coupled to linear optical sensor 112 through color gradient filter 110. In this embodiment, color gradient filter 110 may consist of series of narrow strips of cut-off type filters on a transparent or open substrate, which are constructed so as to positionally correspond to the sensor areas of linear optical sensor 112. An example of a commercially available linear optical sensor 112 is Texas Instruments part number TSL213, which has 61 photo diodes in a linear array. Light receiver fiber optics 7 are arranged correspondingly in a line over linear optical sensor 112. The number of receiver fiber optics may be chosen for the particular application, so long as enough are included to more or less evenly cover the full length of color gradient filter 110. With this embodiment, the light is received and output from receiver fiber optics 7, and the light received by linear optical sensor 112 is integrated for a short period of time (determined by the light intensity, filter characteristics and desired accuracy). The output of linear array sensor 112 is digitized by ADC 114 and output to microprocessor 116 (which may the same processor as microprocessor 10 or another processor).

In general, with the embodiment of FIG. 11, perimeter receiver fiber optics may be used as with the embodiment of FIG. 1, and in general the process described with reference to FIG. 6 is applicable to this embodiment.

Figure 12:
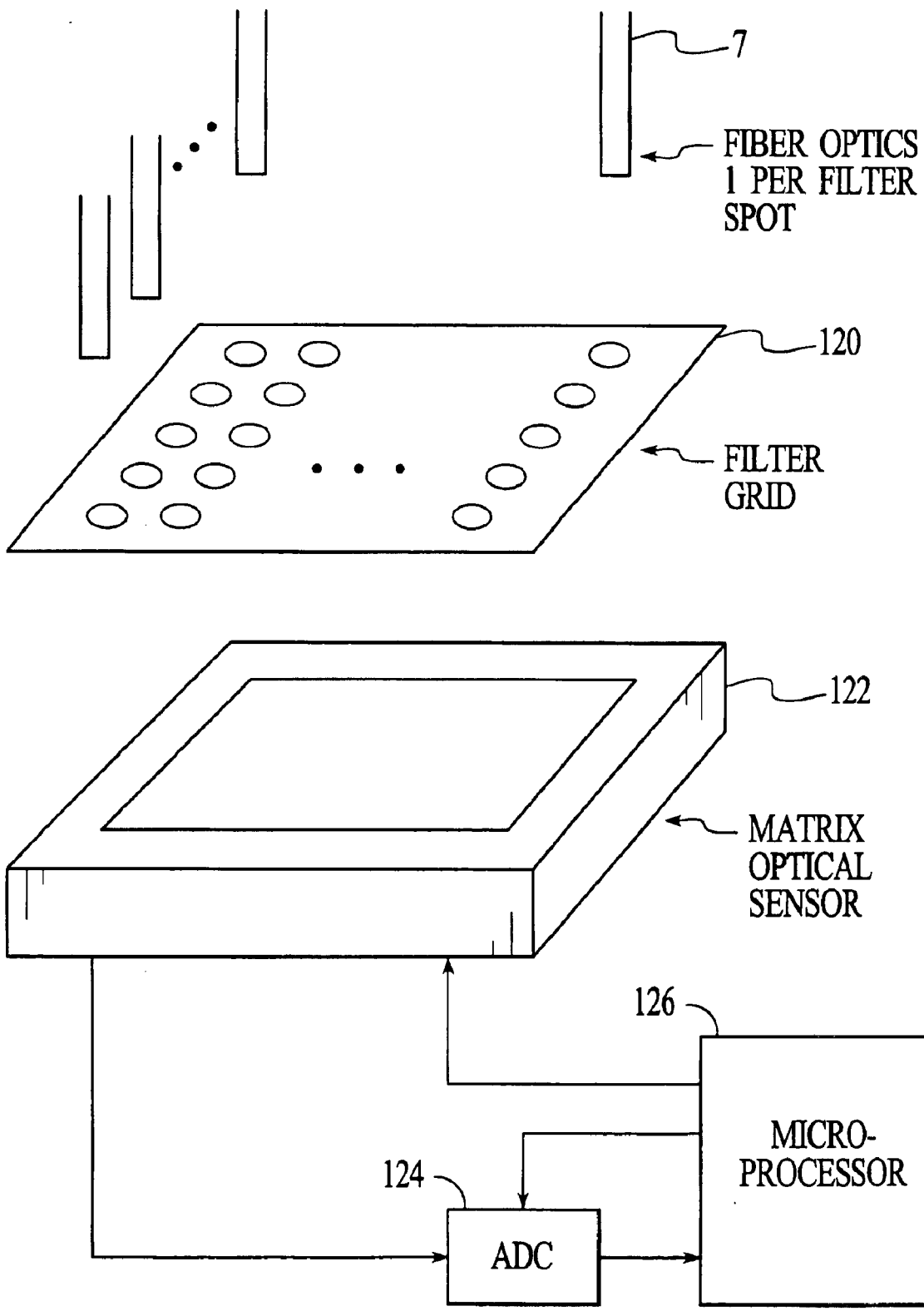
FIG. 12 illustrates a matrix optical sensor array that may be used in certain embodiments of the present invention.

FIG. 12 illustrates an embodiment of the present invention in which a matrix optical sensor and a color filter grid are utilized instead of light sensors 8 (and filters 22, etc.). Receiver fiber optics 7, which may be optically coupled to probe tip 1 as with the embodiment of FIG. 1, are optically coupled to matrix optical sensor 122 through filter grid 120. Filter grid 120 is a filter array consisting of a number of small colored spot filters that pass narrow bands of visible light. Light from receiver fiber optics 7 pass through corresponding filter spots to corresponding points on matrix optical sensor 122. In this embodiment, matrix optical sensor 122 may be a monochrome optical sensor array, such as CCD-type or other type of light sensor element such as may be used in a video camera. The output of matrix optical sensor 122 is digitized by ADC 124 and output to microprocessor 126 (which may the same processor as microprocessor 10 or another processor). Under control of microprocessor 126, matrix optical sensor 126 collects color data from receiver fiber optics 7 through color filter grid 120.

In general, with the embodiment of FIG. 12, perimeter receiver fiber optics may be used as with the embodiment of FIG. 1, and in general the process described with reference to FIG. 6 also is applicable to this embodiment.

As will be clear from the foregoing description, with the present invention a variety of types of spectral color photometers (or tristimulus-type colorimeters) may be constructed, with perimeter receiver fiber optics used to collect color data essentially free from height and angular deviations. In addition, in certain embodiments, the present invention enables color measurements to be taken at a critical height from the surface of the object being measured, and thus color data may be taken without physical contact with the object being measured (in such embodiments, the color data is taken only by passing the probe through region 1 and into region 2, but without necessarily going into region 3 of FIGS. 5A and 5B). Such embodiments may be utilized if contact with the surface is undesirable in a particular application. In the embodiments described earlier, however, physical contact (or near physical contact) of the probe with the object may allow all five regions of FIGS. 5A and 5B to be utilized, thereby enabling color measurements to be taken such that translucency information also may be obtained. Both types of embodiments generally are within the scope of the invention described herein.

Figure 13A:
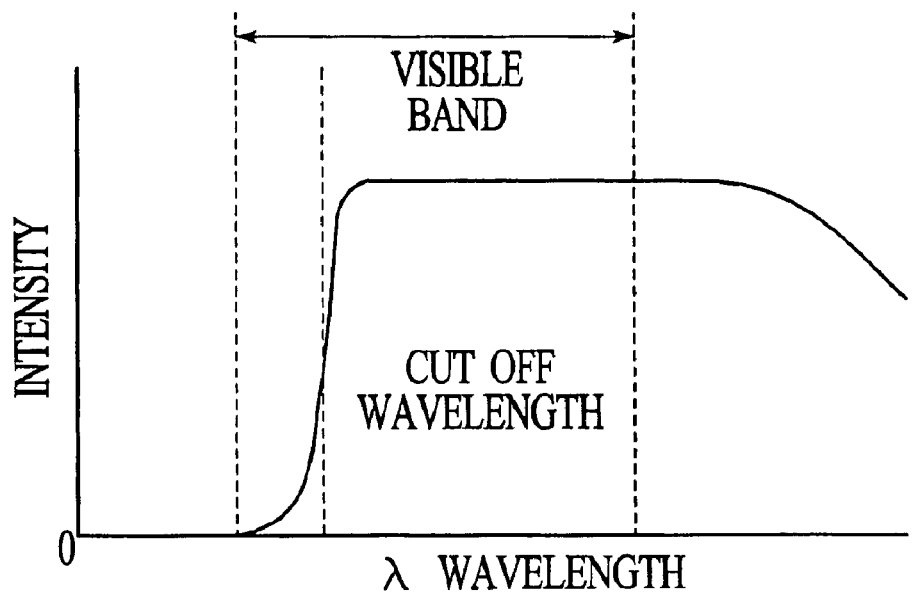
FIGS. 13A and 13B illustrate certain optical properties of a filter array that may be used in certain embodiments of the present invention.
Figure 13B:
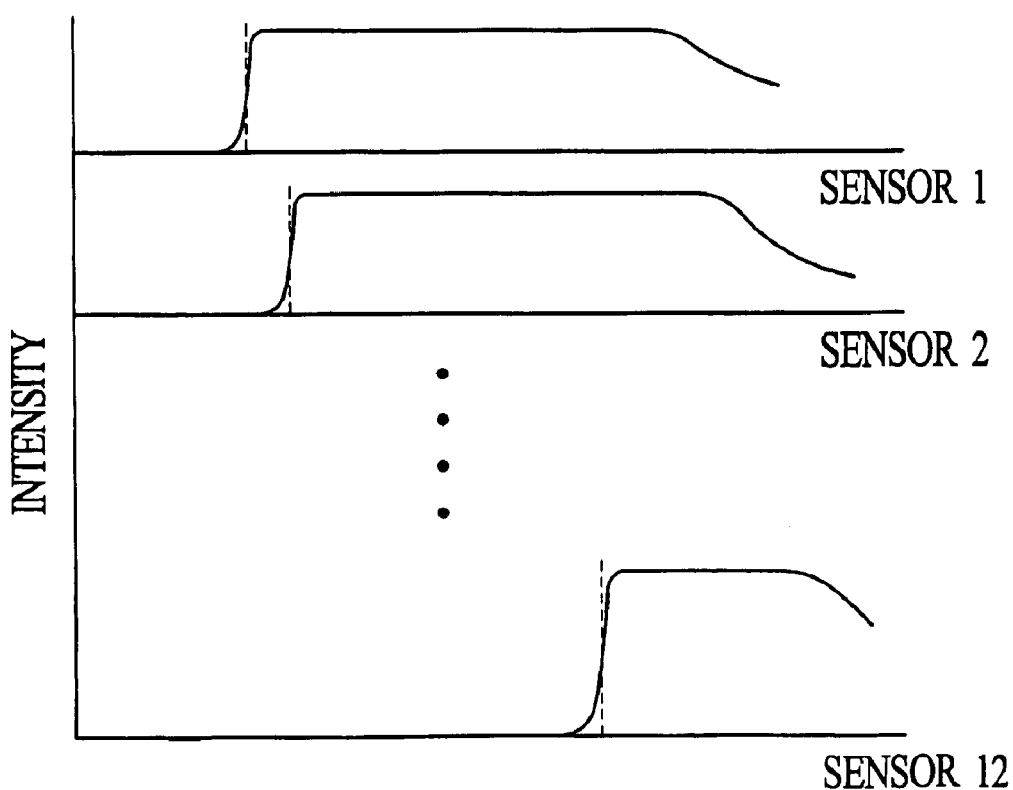

Additional description will now be provided with respect to cut-off filters of the type described in connection with the preferred embodiment(s) of FIGS. 1 and 3 (such as filters 22 of FIG. 3). FIG. 13A illustrates the properties of a single Kodak Sharp Cutting Wratten Gelatin Filter discussed in connection with FIG. 3. Such a cut-off filter passes light below a cut-off frequency (i.e., above a cut-off wavelength). Such filters may be manufactured to have a wide range of cut-off frequencies/wavelengths. FIG. 13B illustrates a number of such filters, twelve in a preferred embodiment, with cut-off frequencies/wavelengths chosen so that essentially the entire visible band is covered by the collection of cut-off filters.

Figure 14A:
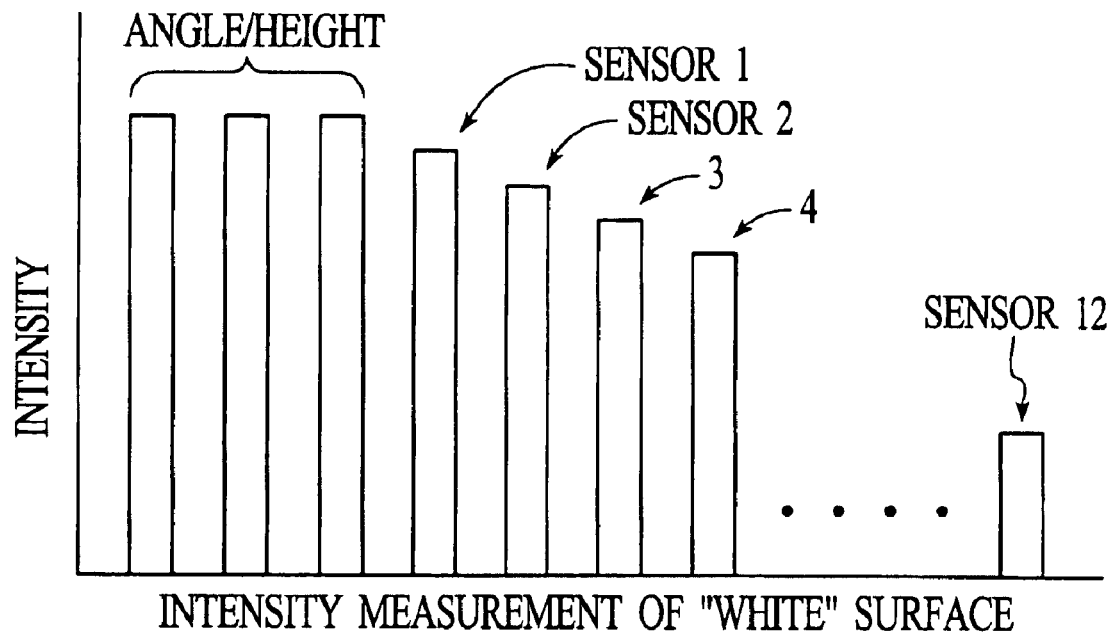
FIGS. 14A and 14B illustrate examples of received light intensities of receivers used in certain embodiments of the present invention.
Figure 14B:
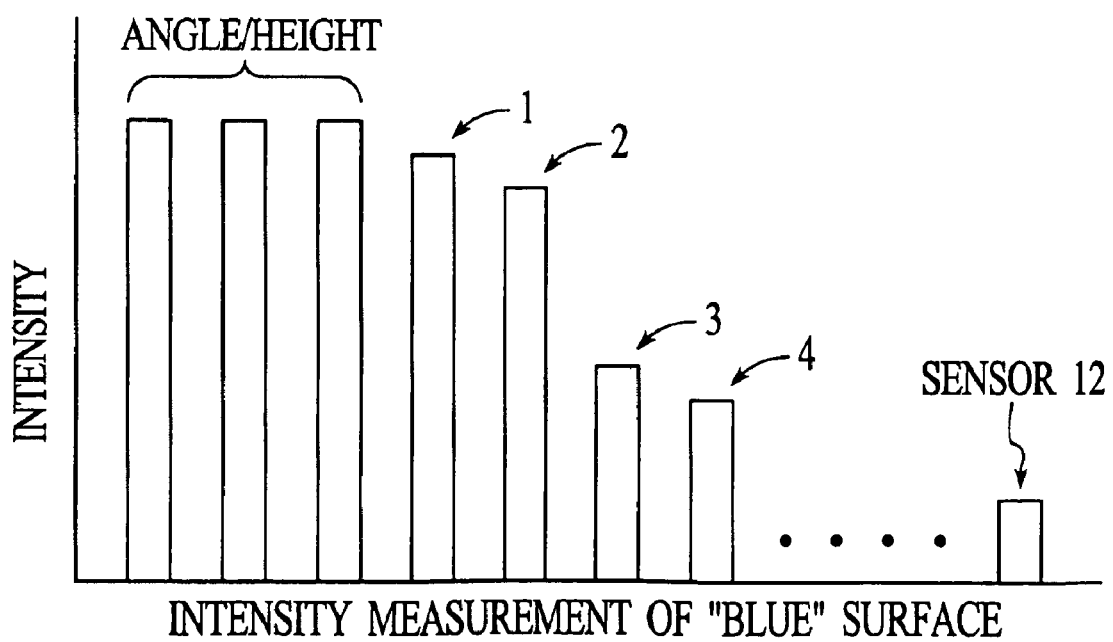

FIGS. 14A and 14B illustrate exemplary intensity measurements using a cut-off filter arrangement such as illustrated in FIG. 13B, first in the case of a white surface being measured (FIG. 14A), and also in the case of a blue surface being measured (FIG. 14B). As illustrated in FIG. 14A, in the case of a white surface, the neutrally filtered perimeter fiber optics, which are used to detect height and angle, etc., generally will produce the highest intensity (although this depends at least in part upon the characteristics of the neutral density filters). As a result of the stepped cut-off filtering provided by filters having the characteristics illustrated in FIG. 13B, the remaining intensities will gradually decrease in value as illustrated in FIG. 14A. In the case of a blue surface, the intensities will decrease in value generally as illustrated in FIG. 14B. Regardless of the surface, however, the intensities out of the filters will always decrease in value as illustrated, with the greatest intensity value being the output of the filter having the lowest wavelength cut-off value (i.e., passes all visible light up to blue), and the lowest intensity value being the output of the filter having the highest wavelength cut-off (i.e., passes only red visible light). As will be understood from the foregoing description, any color data detected that does not fit the decreasing intensity profiles of FIGS. 14A and 14B may be detected as an abnormality, and in certain embodiments detection of such a condition results in data rejection, generation of an error message or initiation of a diagnostic routine, etc.

Reference should be made to the FIGS. 1 and 3 and the related description for a detailed discussion of how such a cut-off filter arrangement may be utilized in accordance with the present invention.

Figure 15:
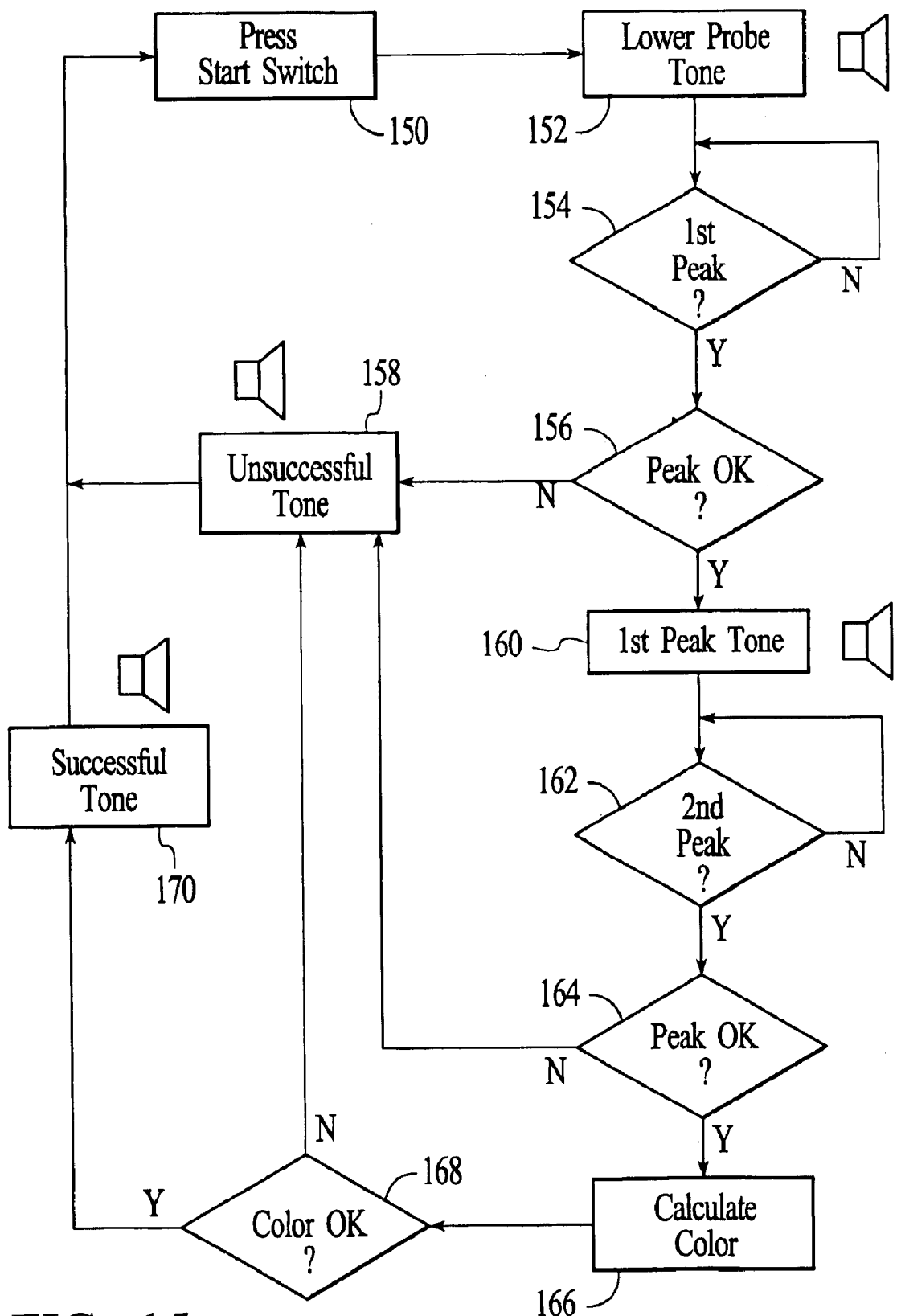
FIG. 15 is a flow chart illustrating audio tones that may be used in certain preferred embodiments of the present invention.

FIG. 15 is a flow chart illustrating audio tones that may be used in certain preferred embodiments of the present invention. It has been discovered that audio tones (such as tones, beeps, voice or the like such as will be described) present a particularly useful and instructive means to guide an operator in the proper use of a color measuring system of the type described herein.

The operator may initiate a color measurement by activation of a switch (such as switch 17 of FIG. 1) at step 150. Thereafter, if the system is ready (set-up, initialized, calibrated, etc.), a lower-the-probe tone is emitted (such as through speaker 16 of FIG. 1) at step 152. The system attempts to detect peak intensity P1 at step 154. If a peak is detected, at step 156 a determination is made whether the measured peak P1 meets the applicable criteria (such as discussed above in connection with FIGS. 5A, 5B and 6). If the measured peak P1 is accepted, a first peak acceptance tone is generated at step 160. If the measured peak P1 is not accepted, an unsuccessful tone is generated at step 158, and the system may await the operator to initiate a further color measurement. Assuming that the first peak was accepted, the system attempts to detect peak intensity P2 at step 162. If a second peak is detected, at step 164 a determination is made whether the measured peak P2 meets the applicable criteria. If the measured peak P2 is accepted the process proceeds to color calculation step 166 (in other embodiments, a second peak acceptance tone also is generated at step 166). If the measured peak P2 is not accepted, an unsuccessful tone is generated at step 158, and the system may await the operator to initiate a further color measurement. Assuming that the second peak was accepted, a color calculation is made at step 166 (such as, for example, microprocessor 10 of FIG. 1 processing the data output from light sensors 8, etc.). At step 168, a determination is made whether the color calculation meets the applicable criteria. If the color calculation is accepted, a successful tone is generated at step 170. If the color calculation is not accepted, an unsuccessful tone is generated at step 158, and the system may await the operator to initiate a further color measurement.

With unique audio tones presented to an operator in accordance with the particular operating state of the system, the operator's use of the system may be greatly facilitated. Such audio information also tends to increase operator satisfaction and skill level, as, for example, acceptance tones provide positive and encouraging feedback when the system is operated in a desired manner.

The color measuring systems and methods in accordance with the present invention may be applied to particular advantage in the field of dentistry, as will be more fully explained hereinafter. In particular the present invention includes the use of such systems and methods to measure the color and other attributes of a tooth in order to prepare a dental prosthesis or intraoral tooth-colored fillings, or to select denture teeth or to determine a suitable cement color for porcelain/resin prostheses. The present invention also provides methods for storing and organizing measured data such as in the form of a patient database.

Figure 16:
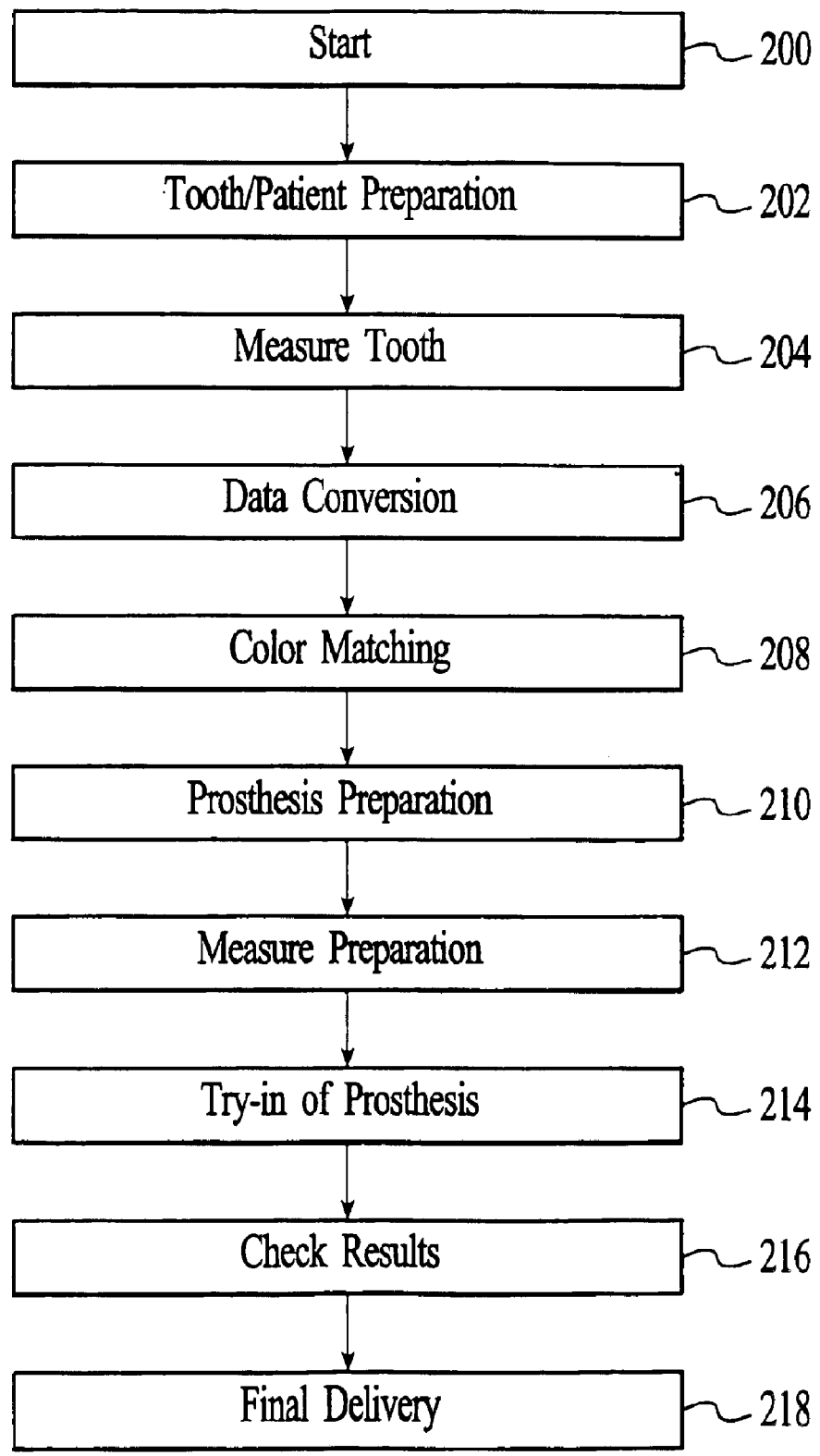
FIG. 16 is a flow chart illustrating a dental prosthesis manufacturing method in accordance with a preferred embodiment of the present invention.

FIG. 16 is a flow chart illustrating a general dental application process flow for use of the color measuring systems and methods in accordance with the present invention. At step 200, the color measuring system may be powered-up and stabilized, with any required initialization or other setup routines performed. At step 200, an indication of the system status may be provided to the operator, such as through LCD 14 or speaker 16 of FIG. 1. Also at step 200, the probe tip may be shielded or a clean probe tip may be inserted in order to reduce the likelihood of contamination (see, e.g., FIGS. 7A to 8B and related description). In other embodiments, a plastic or other shield may also be used, so long as it is constructed and/or positioned so as to not adversely affect the measurement process.

Figure 17A:
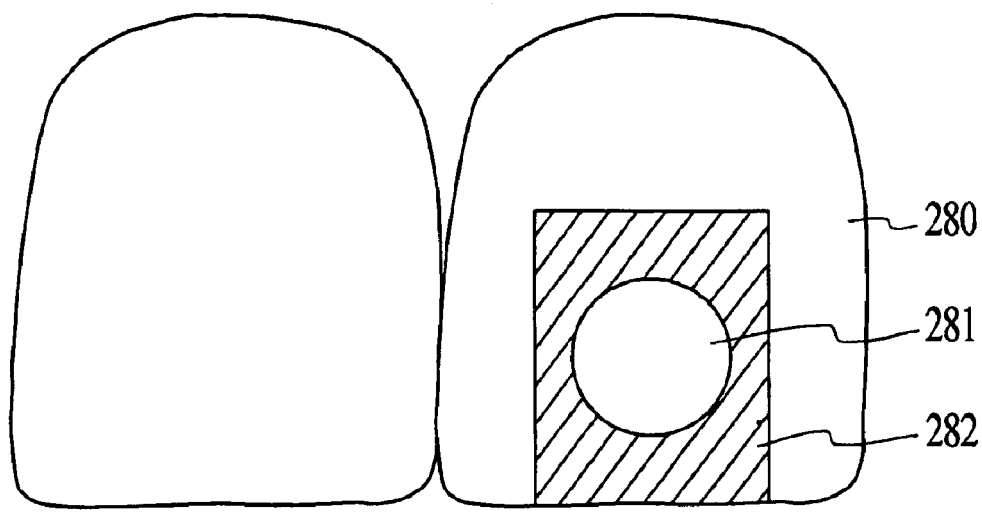
FIGS. 17A and 17B illustrate a positioning implement used in certain embodiments of the present invention.
Figure 17B:
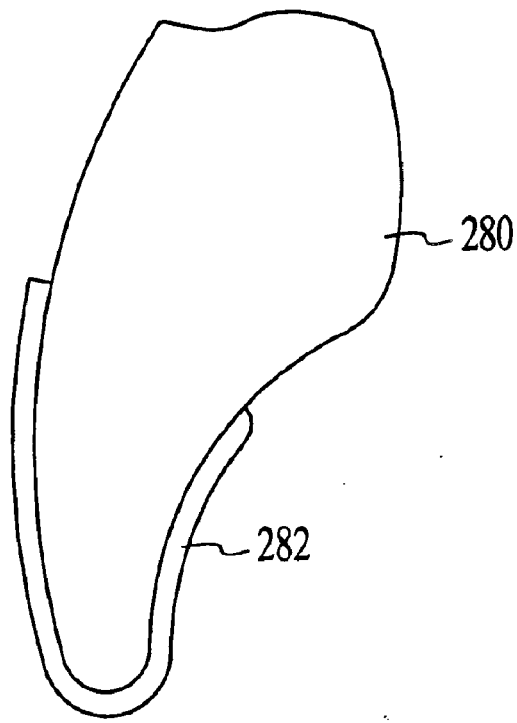

At step 202, the patient and the tooth to be measured are prepared. Any required cleaning or other tooth preparation would be performed at step 202. Any required patient consultation about the type of prosthesis or area of a tooth to be matched would be performed at (or before) step 202. In certain embodiments, a positioning device is prepared at step 202, such as is illustrated in FIGS. 17A and 17B. In such embodiments, for example, a black or other suitably-colored material 282, which may adhere to tooth 280 (such as with a suitable adhesive), is formed to have opening 281 larger than the diameter of the measuring probe, with opening 281 centered on the area of tooth 280 to be measured. The material of positioning device 282 is formed in a manner to fit on/over tooth 280 (such as over the incisal edge of tooth 280 and/or over one or more adjacent teeth) so that it may be placed on/over tooth 280 in a repeatable manner. Such a positioning device may serve to ensure that the desired area of tooth 280 is measured, and also allows for repeat measurements of the same area for purposes of confirmation or the like. Any other pre-measurement activities may be performed at (or before) step 202.

At step 204, the operator (typically a dentist or other dental professional) moves the probe towards the area of the tooth to be measured. This process preferably is conducted in accordance with the methodology described with reference to FIGS. 5A, 5B and 6, and preferably is accompanied by audio tones such as described with reference to FIG. 15. With the present invention, the operator may obtain color and translucency data, for example, from a desired area of the tooth to be measured. During step 204, an accepted color measurement is made, or some indication is given to the operator that the measurement step needs to be repeated or some other action taken. After an accepted color measurement is made at step 204, for example, the dentist may operate on the desired tooth or teeth or take other action. Before or after such action, additional measurements may be taken as needed (see, e.g., FIG. 18 and related description).

Upon successful completion of one or more measurements taken at step 204, the process proceeds to step 206. At step 206, any data conversion or processing of data collected at step 204 may be performed. For example, in the embodiment of FIG. 1, detailed color spectrum and translucency information is generated. In a particular dental application, however, it may be that a dental lab, for example, requires that the color be presented in Munsell format (i.e., chroma, hue and value), RGB values, XYZ coordinates, CIELAB values, Hunter values, or some other color data format. With the spectral/color information produced by the present invention, data may be converted to such formats through conventional matrix math, for example. Such math may be performed by microprocessor 10 or computer 13A of FIG. 1, or in some other manner. It also should be noted that, in certain embodiments, the data produced at step 204 in accordance with the present invention may be used directly without data conversion. In such embodiments, step 206 may be omitted. In other embodiments, step 206 consists of data formatting, such as preparing the data for reproduction in hard copy, pictorial or other form, or for transmission as facsimile or modem data. Finally, in certain embodiments a translucency factor is computed in a format suitable for the particular application. In yet other embodiments, a surface texture or detail factor is computed in a format suitable for the particular application.

At step 208, a matching is optionally attempted between the data produced at steps 204 and 206 (if performed) and a desired color (in other embodiments, the process may proceed from 204 directly to 210, or alternatively steps 206 and 208 may be combined). For example, a number of "shade guides" are available in the market, some of which are known in the industry as Vita shade guides, Bioform shade guides or other color matching standards, guides or references or custom shade guides. In certain preferred embodiments, a lookup table is prepared and loaded into memory (such as memory associated with microprocessor 10 or computer 13A of FIG. 1), and an attempt is made to the closest match or matches of the collected data with the known shade guides, custom shade guides or reference values. In certain embodiments, a translucency factor and/or a surface texture or detail factor also is used in an effort to select the best possible match.

In a particular aspect of certain embodiments of the present invention, at step 208 a material correlation lookup table is accessed. Based on the color and translucency data obtained at step 204, a proposed recipe of materials, pigments or other instruction information is prepared for a prosthesis or filling, etc., of the desired color and translucency, etc. With the detailed color and other information made available in accordance with the present invention, a direct correlation with the relevant constituent materials may be made. In still other embodiments, such information is made available to an automated mixing or manufacturing machine for preparation of prosthesis or material of the desired color and translucency, as more fully described elsewhere herein.

At step 210, based on the results of the preceding steps, the prosthesis, denture, intraoral tooth-colored filling material or other items are prepared. This step may be performed at a dental lab, or, in certain embodiments, at or near the dental operatory. For remote preparation, relevant data produced at steps 204, 206 and/or 208 may be sent to the remote lab or facility by hardcopy, facsimile or modem or other transmission. What should be understood from the foregoing is that, based on data collected at step 204, a prosthesis may be prepared of a desirable color at step 210.

At step 212, the prosthesis or other material prepared at step 210 may be measured for confirmation purposes, again preferably conducted in accordance with the methodology described with reference to FIGS. 5A, 5B and 6, and preferably accompanied by audio tones such as described with reference to FIG. 15. A re-measure of the tooth in the patient's mouth, etc. also may be made at this step for confirmation purposes. If the confirmation process gives satisfactory results, the prosthesis, denture, composite filling or other material may be preliminarily installed or applied in the patient at step 214. At step 216, a re-measure of the prosthesis, denture, composite filling or other materials optionally may be made. If the results of step 216 are acceptable, then the prosthesis may be more permanently installed or applied in the patient at step 218. If the results of step 216 are not acceptable, the prosthesis may be modified and/or other of the steps repeated as necessary in the particular situation.

Figure 18:
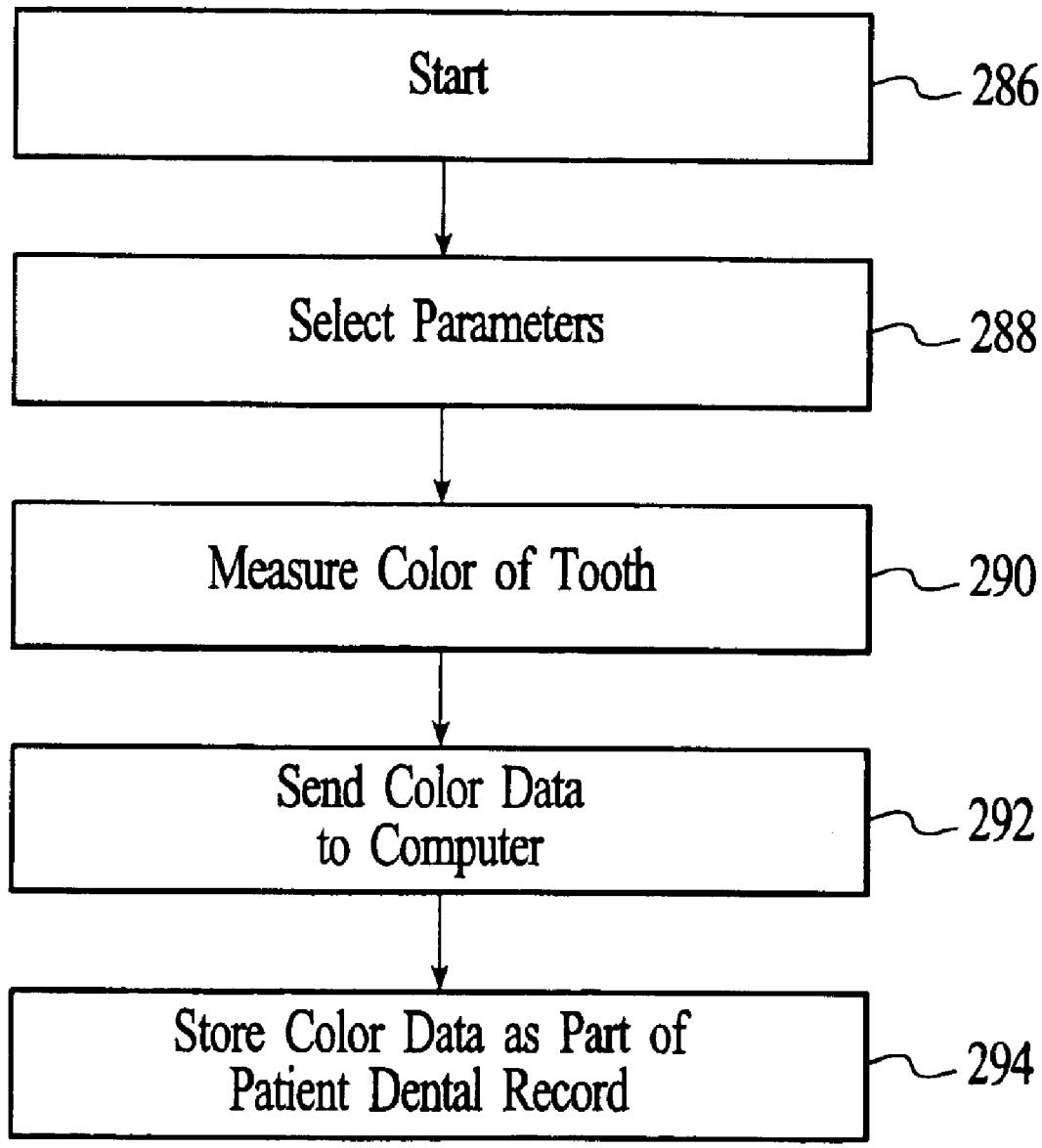
FIG. 18 is a flow chart illustrating a patient database method in accordance with certain embodiments of the present invention.

In another particular aspect of the present invention, for example, data processing such as illustrated in FIG. 18 may be taken in conjunction with the process of FIG. 16. At step 286, client database software is run on a computing device, such as computer 13A of FIG. 1. Such software may include data records for each patient, including fields storing the history of dental services performed on the patient, information regarding the status or condition of the patient's teeth, billing, address and other information. Such software may enter a mode by which it is in condition to accept color or data take in accordance with the present invention.

At step 288, for example, the dentist or other dental professional may select parameters for a particular tooth of the patient to be measured. Depending on the size and condition of the tooth (such as color gradient or the like), the dentist may sector the tooth into one or more regions, such as a grid. Thus, for example, in the case of tooth for which it is decided to take four measurements, the tooth may be sectored into four regions. Such parameters, which may include a pictorial representation on the computer of the tooth sectored into four regions (such as by grid lines), along with tooth identification and patient information may be entered into the computer at this time.

At step 290, one or more measurements of the tooth may be taken, such as with a system and method as described in connection with FIGS. 1, 5A, 5B and/or 6. The number of such measurements preferably is associated with the parameters entered at step 288. Thereafter, at step 292, the data collected from the measurement(s) may be sent to the computer for subsequent processing. As an illustrative example, four color measurements may be taken (for the four regions of the tooth in the above example) and sent to the computer, with the data for the four color measurements (such as RGB or other values) associated with the four regions in accordance with the entered parameters. Also as an example, the displayed pictorial representation of the tooth may have overlaid thereof data indicative of the color measurement(s). At step 294, such as after completion of color measurements on the particular patient, the data collected during the process may be associatively stored as a part of the patient's dental records in the data base. In embodiments accompanied by use of an intraoral camera, for example (see, e.g., FIG. 19 and related description), captured images of one or more of the patient's teeth also may be associatively stored as part of the patient's dental records. In certain embodiments, a picture captured by the intraoral camera is overlaid with grid or sector lines (such as may be defined in step 288), with color or other data measured as described herein also overlaid over the captured image. In such a manner, the color or other data may be electronically and visually associated with a picture of the particular measured tooth, thereby facilitating the use of the system and the understanding of the collected data. In still other embodiments, all such captured image and color measurement records include a time and/or date, so that a record of the particular history of a particular tooth of a particular patient may be maintained.

Figure 19:
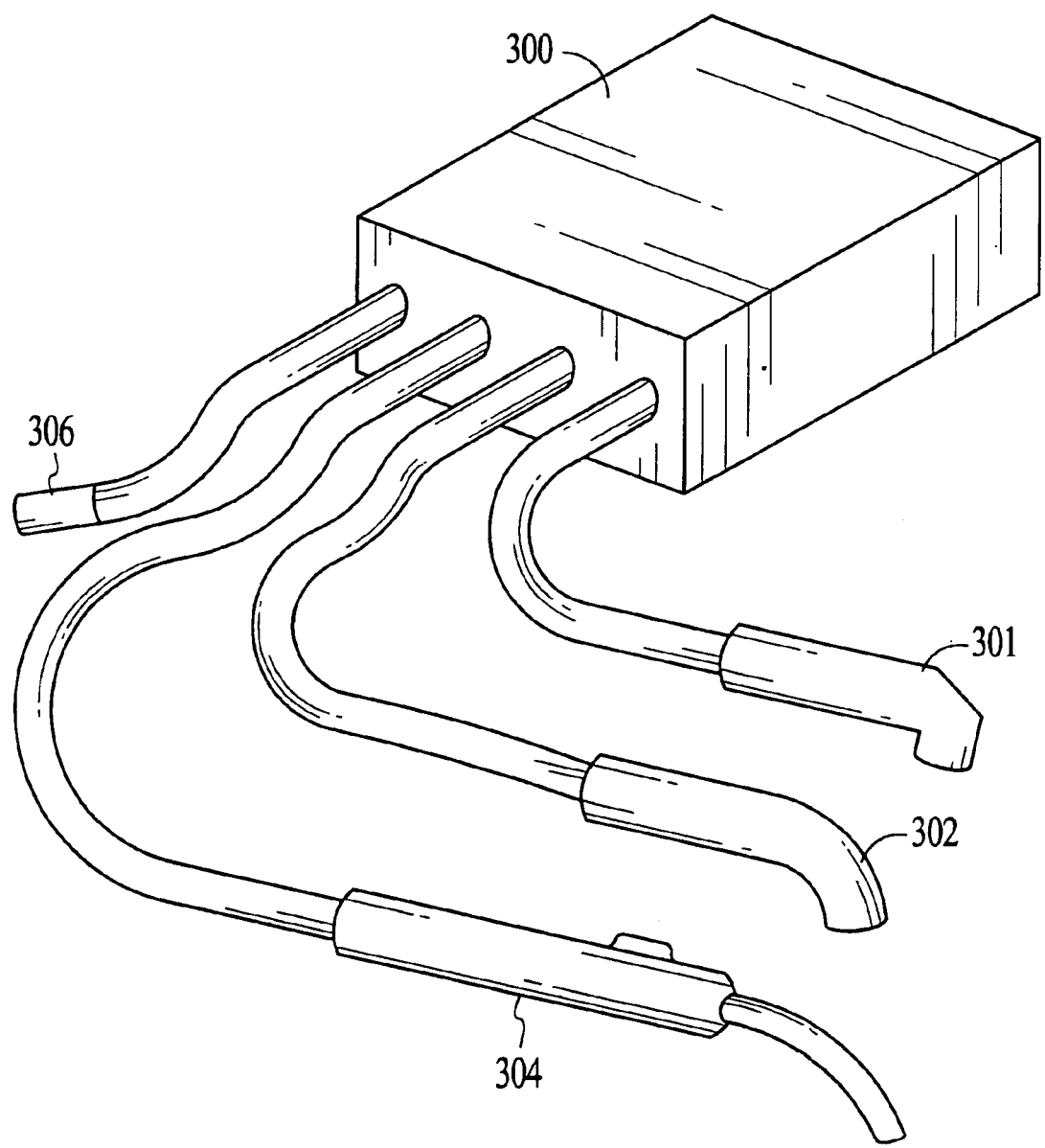
FIG. 19 illustrates an integrated unit in accordance with the present invention that includes a measuring device and other implements.

In yet another particular aspect of the present invention, a measuring device and method (such as described elsewhere herein) may be combined with an intraoral camera and other implements. As illustrated in FIG. 19, control unit 300 contains conventional electronics and circuitry, such as power supplies, control electronics, light sources and the like. Coupled to control unit 300 is intraoral camera 301 (for viewing, and capturing images of, a patient's tooth or mouth, etc.), curing light 302 (such as for curing light-cured intraoral filling material), measuring device 304 (such as described elsewhere herein), and visible light 306 (which may be an auxiliary light for intraoral examinations and the like). With such embodiments, color, translucency, fluorescence, surface texture and/or other data collected for a particular tooth from measuring device 304 may be combined with images captured by intraoral camera 301, with the overall examination and processing of the patient facilitated by having measuring device 304, intraoral camera 301, curing light 302 and visible light 306 integrated into a single unit. Such integration serves to provide synergistic benefits in the use of the instruments, while also reducing costs and saving physical space. In another particular aspect of such embodiments, the light source for measuring device 304 and intraoral camera 301 are shared, thereby resulting in additional benefits.

As will be apparent to those skilled in the art, certain refinements may be made in accordance with the present invention. For example, a central light source fiber optic is utilized in certain preferred embodiments, but other light source arrangements (such as a plurality of light source fibers, etc.). In addition, lookup tables are utilized for various aspects of the present invention, but polynomial type calculations could similarly be employed. Thus, although various preferred embodiments of the present invention have been disclosed for illustrative purposes, those skilled in the art will appreciate that various modifications, additions and/or substitutions are possible without departing from the scope and spirit of the present invention as disclosed in the claims.

Reference is also made to copending application Ser. No. 08/909,666, filed Jan. 2, 1996, for "Apparatus and Method for Measuring Color," by the inventors hereof, which is hereby incorporated by reference.

What is claimed is:

1. A method of determining the optical characteristics of a dental object with an integrated system including a camera and a spectrophotometer, comprising the steps of:
   generating an image of the dental object with the camera of the integrated system;
   software processing the image of the dental object to determine a plurality of regions of the dental object that have different optical characteristics; and
   generating optical characteristics data indicative of the optical characteristics of the dental object in one or more of the plurality of regions with the spectrophotometer of the integrated system.

2. The method of claim 1, wherein the method further comprises the step of calibrating the spectrophotometer by taking a measurement of a calibration standard.

3. The method of claim 1, wherein the spectrophotometer measures light returned from the dental object in a plurality of spectral bands.

4. The method of claim 1, wherein the integrated system operates with audio feedback, wherein the audio feedback guides a user's operation of the integrated system.

5. The method of claim 1, wherein the optical characteristics data are stored in a database, wherein the optical characteristics data are generated a plurality of times for a plurality of dental objects to generate a plurality of optical characteristics database records.

6. The method of claim 5, where in the database records are associated with particular patients.

7. The method of claim 5, wherein the database records store pictures of the dental objects.

8. The method of claim 7, wherein the pictures of the dental objects comprise images of the dental objects captured with the camera.

9. The method of claim 5, wherein the optical characteristics data are generated a plurality of times for the dental object, wherein a database stores a historical record of the optical characteristics of the dental object.

10. The method of claim 1, wherein a second dental object is produced based on the optical characteristics data.

11. The method of claim 10, wherein optical characteristics of the second dental object are determined prior to installation of the second dental object in a patient's mouth.

12. The method of claim 11, wherein the optical characteristics of the second dental object are determined with the integrated system or a second integrated system.

13. The method of claim 11, wherein the optical characteristics of the second dental object are determined at a location where the second dental object is produced.

14. The method of claim 13, wherein the optical characteristics of the second dental object are determined with a second integrated system.

15. The method of claim 11, wherein the optical characteristics of the second dental object are determined at a location wherein the second dental object is to be installed in the patient's mouth.

16. The method of claim 15, wherein the optical characteristics of the second dental object are determined with the integrated system.

17. The method of claim 10, wherein the second dental object comprises a denture.

18. The method of claim 10, wherein the second dental object comprises a dental prosthesis.

19. The method of claim 10, wherein the second dental object comprises a filling.

20. The method of claim 10, wherein the second dental object comprises a tooth-colored filling.

21. The method of claim 10, wherein the second dental object comprises a composite filling.

22. The method of claim 10, wherein the second dental object is produced based on a porcelain recipe determined in accordance with the optical characteristics data.

23. The method of claim 1, wherein the optical characteristics data are electronically transmitted to a remote location, wherein a second object is produced at the remote location based on the transmitted optical characteristics data.

24. The method of claim 23, wherein the electronic transmission comprises a modem transmission.

25. The method of claim 23, wherein the electronic transmission includes a transmission of a picture of the dental object.

26. The method of claim 25, wherein the picture of the dental object comprises an image of the dental object captured with the camera.

27. The method of claim 1, wherein the optical characteristics data are stored in a database, wherein the database includes date and time information associated with the optical characteristics data.

28. The method of claim 1, wherein the optical characteristics data are stored in a database, wherein optical characteristics data indicative of the optical characteristics are generated a plurality of times, including at least once for a plurality of the regions.

29. The method of claim 28, wherein the database stores sectoring information with the optical characteristics data.

30. The method of claim 29, wherein the database stores information corresponding to a pictorial representation of the dental object that includes sector grid lines.

31. The method of claim 1, wherein a material mixing unit receives the optical characteristics data, wherein the material mixing unit prepares constituent materials for a second dental object based on the optical characteristics data.

32. The method of claim 1, wherein the camera comprises an intraoral camera.

33. The method of claim 1, wherein the camera comprises a video camera.

34. The method of claim 1, wherein the optical characteristics data is output in the form of a closest match or matches to one or a plurality of sets of stored shade guide values.

35. The method of claim 1, wherein a computing system stores data corresponding to a plurality of shade guide systems, each of the plurality of shade guide systems having a plurality of shade guide values, wherein the optical characteristics data is output in the form of a closest match or matches to one or more of the shade guide values in the plurality of shade guide systems.

36. The method of claim 35, wherein the optical characteristics data is output in the form of the closest match to one of the shade guide values in the plurality of shade guide systems.

37. The method of claim 1, wherein the optical characteristics data is used to electronically output a proposed recipe of materials for preparing a second dental object.

38. The method of claim 37, wherein the optical characteristics data is used to electronically output a proposed recipe of materials and instruction information for preparing a second dental object.

39. The method of claim 1, wherein the optical characteristics data is output in the form of one or more sets of color tri-stimulus values.

40. The method of claim 1, wherein an image of the dental object is displayed, wherein data indicative of the color of the dental object in one or more particular regions of the plurality of regions are displayed in an overlaid manner over the one or more particular regions.

41. A method of determining the optical characteristics of a dental object with an integrated system including a camera and a spectrophotometer, comprising the steps of:
generating an image of the dental object with the camera of the integrated system;
software processing the image of the dental object; and
generating optical characteristics data indicative of the optical characteristics of the dental object in one or more of regions of the dental object with the spectrophotometer of the integrated system.

42. The method of claim 41, wherein the method further comprises the step of calibrating the spectrophotometer by taking a measurement of a calibration standard.

43. The method of claim 41, wherein the spectrophotometer measures light returned from the dental object in a plurality of spectral bands.

44. The method of claim 41, wherein the integrated system operates with audio feedback, wherein the audio feedback guides a user's operation of the integrated system.

45. The method of claim 41, wherein the optical characteristics data are stored in a database, wherein the optical characteristics data are generated a plurality of times for a plurality of dental objects to generate a plurality of optical characteristics database records.

46. The method of claim 45, wherein the database records are associated with particular patients.

47. The method of claim 45, wherein the database records store pictures of the dental objects.

48. The method of claim 47, wherein the pictures of the dental objects comprise images of the dental objects captured the camera.

49. The method of claim 45, wherein the optical characteristics data are generated a plurality of times for the dental object, wherein a database stores a historical record of the optical characteristics of the dental object.

50. The method of claim 41, wherein a second dental object is produced based on the optical characteristics data.

51. The method of claim 50, wherein optical characteristics of the second dental object are determined prior to installation of the second dental object in a patient's mouth.

52. The method of claim 51, wherein the optical characteristics of the second dental object are determined with the integrated system or a second integrated system.

53. The method of claim 51, wherein the optical characteristics of the second dental object are determined at a location where the second dental object is produced.

54. The method of claim 53, wherein the optical characteristics of the second dental object are determined with a second integrated system.

55. The method of claim 51, wherein the optical characteristics of the second dental object are determined at a location wherein the second dental object is to be installed in the patient's mouth.

56. The method of claim 55, wherein the optical characteristics of the second dental object are determined with the integrated system.

57. The method of claim 50, wherein the second dental object comprises a denture.

58. The method of claim 50, wherein the second dental object comprises a dental prosthesis.

59. The method of claim 50, wherein the second dental object comprises a filling.

60. The method of claim 50, wherein the second dental object comprises a tooth-colored filling.

61. The method of claim 50, wherein the second dental object comprises a composite filling.

62. The method of claim 50, wherein the second dental object is produced based on a porcelain recipe determined in accordance with the optical characteristics data.

63. The method of claim 41, wherein the optical characteristics data are electronically transmitted to a remote location, wherein a second dental object is produced at the remote location based on the transmitted optical characteristics data.

64. The method of claim 63, wherein the electronic transmission comprises a modem transmission.

65. The method of claim 63, wherein the electronic transmission includes a transmission of a picture of the dental object.

66. The method of claim 65, wherein the picture of the dental object comprises an image of the dental object captured with the camera.

67. The method of claim 41, wherein the optical characteristics data are stored in a database, wherein the database includes date and time information associated with the optical characteristics data.

68. The method of claim 41, wherein the optical characteristics data are stored in a database, wherein optical characteristics data indicative of the optical characteristics are generated a plurality of times, including at least once for a plurality of regions of the dental object.

69. The method of claim 68, wherein the database stores sectoring information with the optical characteristics data.

70. The method of claim 69, wherein the database stores information corresponding to a pictorial representation of the dental object that includes sector grid lines.

71. The method of claim 41, wherein a material mixing unit receives the optical characteristics data, wherein the material mixing unit prepares constituent materials for a second dental object based on the optical characteristics data.

72. The method of claim 41, wherein the camera comprises an intraoral camera.

73. The method of claim 41, wherein the camera comprises a video camera.

74. The method of claim 41, wherein the optical characteristics data is output in the form of a closest match or matches to one or a plurality of sets of stored shade guide values.

75. The method of claim 41, wherein a computing system stores data corresponding to a plurality of shade guide systems, each of the plurality of shade guide systems having a plurality of shade guide values, wherein the optical characteristics data is output in the form of a closest match or matches to one or more of the shade guide values in the plurality of shade guide systems.

76. The method of claim 75, wherein the optical characteristics data is output in the form of the closest match to one of the shade guide values in the plurality of shade guide systems.

77. The method of claim 41, wherein the optical characteristics data is used to electronically output a proposed recipe of materials for preparing a second dental object.

78. The method of claim 77, wherein the optical characteristics data is used to electronically output a proposed recipe of materials and instruction information for preparing a second dental object.

79. The method of claim 41, wherein the optical characteristics data is output in the form of one or more sets of color tri-stimulus values.

80. The method of claim 41, wherein an image of the dental object is displayed, wherein data indicative of the color of the dental object in one or more particular regions of the dental object are displayed in an overlaid manner over the one or more particular regions.

81. A method of determining the optical characteristics of a dental object with an apparatus that includes an imaging element and a spectrometer apparatus, the method comprising the steps of:
generating an image of the dental object with the imaging element; and
generating optical characteristics data indicative of optical characteristics of the dental object including at least color characteristics with the spectrometer apparatus;
wherein, under software control a determination is made of a plurality of regions of the dental object having different color characteristics;
wherein optical characteristics of the dental object including at least color characteristics are determined in the plurality of regions based on the optical characteristics data generated with the spectrometer apparatus.

82. The method of claim 81, wherein the method further comprises the step of generating optical characteristics data of a color reference standard, wherein the optical characteristics data indicative of optical characteristics of the dental object are generated based on the optical characteristics data of the color reference standard.

83. The method of claim 81, wherein the spectrometer apparatus measures light returned from the dental object in a plurality of spectral bands.

84. The method of claim 81, wherein audio feedback is generated, wherein the audio feedback guides a user's operation of the apparatus.

85. The method of claim 81, wherein the optical characteristics data are stored in a database, wherein the optical characteristics data are generated a plurality of times for a plurality of dental objects to generate a plurality of optical characteristics database records.

86. The method of claim 85, wherein the database records are associated with particular patients.

87. The method of claim 85, wherein the database records store images representative of the dental objects.

88. The method of claim 87, wherein the images representative of the dental objects comprise images of the dental objects captured with the imaging element.

89. The method of claim 85, wherein the optical characteristics data are generated a plurality of times for the dental object, wherein a database stores a historical record of the optical characteristics of the dental object.

90. The method of claim 81, wherein a second dental object is produced based on the optical characteristics data.

91. The method of claim 90, wherein optical characteristics of the second dental object are determined prior to installation of the second dental object in a patient's mouth.

92. The method of claim 91, wherein the optical characteristics of the second dental object are determined with the apparat or a second apparatus.

93. The method of claim 91, wherein the optical characteristics of the second dental object are determined at a location where the second dental object is produced.

94. The method of claim 93, wherein the optical characteristics of the second dental object are determined with a second apparatus.

95. The method of claim 91, wherein the optical characteristics of the second dental object are determined at a location wherein the second dental object is to be installed in the patient's mouth.

96. The method of claim 95, wherein the optical characteristics of the second dental object are determined with the apparatus.

97. The method of claim 90, wherein the second dental object comprises a denture.

98. The method of claim 90, wherein the second dental object comprises a dental prosthesis.

99. The method of claim 90, wherein the second dental object comprises a filling.

100. The method of claim 90, wherein the second dental object comprises a tooth-colored filling.

101. The method of claim 90, wherein the second dental object comprises a composite filling.

102. The method of claim 90, wherein the second dental object is produced based on a porcelain recipe determined in accordance with the optical characteristics data.

103. The method of claim 81, wherein the optical characteristics data are electronically transmitted to a remote location, wherein a second object is produced at the remote location based on the transmitted optical characteristics data.

104. The method of claim 103, wherein the electronic transmission comprises a modem transmission.

105. The method of claim 103, wherein the electronic transmission includes a transmission of an image representative of the dental object.

106. The method of claim 105, wherein the image representative of the dental object comprises an image of the dental object captured with the imaging element.

107. The method of claim 81, wherein the optical characteristics data are stored in a database, wherein the database includes date and time information associated with the optical characteristics data.

108. The method of claim 81, wherein the optical characteristics data are stored in a database, wherein optical characteristics data indicative of the optical characteristics are generated a plurality of times, including at least once for a plurality of the regions.

109. The method of claim 108, wherein the database stores sectoring information with the optical characteristics data.

110. The method of claim 109, wherein the database stores information corresponding to a pictorial representation of the dental object that includes sector grid lines.

111. The method of claim 81, wherein a material mixing unit receives the optical characteristics data, wherein the material mixing unit prepares constituent materials for a second dental object based on the optical characteristics data.

112. The method of claim 81, wherein the imaging element comprises an intraoral camera.

113. The method of claim 81, wherein the imaging element comprises a video camera.

114. The method of claim 81, wherein the optical characteristics data is output in the form of a closest match or matches to one or a plurality of sets of stored shade guide values.

115. The method of claim 81, wherein a computing system stores data corresponding to a plurality of shade guide systems, each of the plurality of shade guide systems having a plurality of shade guide values, wherein the optical characteristics data is output in the form of a closest match or matches to one or more of the shade guide values in the plurality of shade guide systems.

116. The method of claim 115, wherein the optical characteristics data is output in the form of the closest match to one of the shade guide values in the plurality of shade guide systems.

117. The method of claim 81, wherein the optical characteristics data is used to electronically output a proposed recipe of materials for preparing a second dental object.

118. The method of claim 117, wherein the optical characteristics data is used to electronically output a proposed recipe of materials and instruction information for preparing a second dental object.

119. The method of claim 81, wherein the optical characteristics data is output in the form of one or more sets of color tri-stimulus values.

120. The method of claim 81, wherein an image of the dental object is displayed, wherein data indicative of the color of the dental object in one or more particular regions of the plurality of regions are displayed in an overlaid manner over the one or more particular regions.

* * * * *